(12) United States Patent
Khosla et al.

(10) Patent No.: US 10,010,541 B2
(45) Date of Patent: Jul. 3, 2018

(54) MODULATION OF TISSUE TRANSGLUTAMINASE ACTIVATION IN DISEASE

(71) Applicant: The Board of Trustees of the Leland Stanford Junior University, Stanford, CA (US)

(72) Inventors: Chaitan Khosla, Palo Alto, CA (US); Thomas DiRaimondo, Orinda, CA (US); Cornelius Kloeck, Kaufbevren (DE)

(73) Assignee: The Board of Trustees of the Leland Stanford Junior University, Stanford, CT (US)

( * ) Notice: Subject to any disclaimer, the term of this patent is extended or adjusted under 35 U.S.C. 154(b) by 0 days.

(21) Appl. No.: 15/114,756

(22) PCT Filed: Jan. 29, 2015

(86) PCT No.: PCT/US2015/013576
§ 371 (c)(1),
(2) Date: Jul. 27, 2016

(87) PCT Pub. No.: WO2015/116846
PCT Pub. Date: Aug. 6, 2015

(65) Prior Publication Data
US 2016/0339012 A1    Nov. 24, 2016

Related U.S. Application Data

(60) Provisional application No. 61/933,711, filed on Jan. 30, 2014.

(51) Int. Cl.
| | |
|---|---|
| *A61K 31/4709* | (2006.01) |
| *A61K 31/4725* | (2006.01) |
| *C07D 413/14* | (2006.01) |
| *A61K 38/44* | (2006.01) |

(52) U.S. Cl.
CPC ...... *A61K 31/4709* (2013.01); *A61K 31/4725* (2013.01); *A61K 38/44* (2013.01); *C07D 413/14* (2013.01); *C12Y 108/0401* (2013.01)

(58) Field of Classification Search
CPC ............ A61K 31/4709; A61K 31/4725; A61K 38/44; C07D 413/14; C12Y 108/0401
See application file for complete search history.

(56) References Cited

U.S. PATENT DOCUMENTS

| | | | |
|---|---|---|---|
| 6,468,977 B1 | 10/2002 | Karimian et al. | |
| 2006/0052308 A1* | 3/2006 | Khosla ................ | A61K 31/42 514/19.3 |
| 2012/0245106 A1 | 9/2012 | Larsen et al. | |

FOREIGN PATENT DOCUMENTS

WO    2012/177640    * 12/2012

OTHER PUBLICATIONS

Watts, J MEd CHem vol. 49(25), 7493-7501, 2006.*
Castelhano et al., "Synthesis, Chemistry, and Absolute Configuration of Novel Transglutaminase Inhibitors Containing a 3-Halo-4,5-dihydroiso, xazole1", Aug. 1988, Bioorganic Chemistry, Pages pp. 335-340, vol. 16, Issue 3, Academic Press, Inc., Cambridge, MA.
Choi et al., "Chemistry and Biology of Dihydroisoxazole Derivatives: Selective Inhibitors of Human Transglutaminase 2", Chem. Biol., Apr. 2005, pp. 469-475, vol. 12, Issue 4, Elsevier Inc., Amsterdam, Netherlands.
Dafik et al., "Dihydroisoxazole Analogs for Labeling and Visualization of Catalytically Active Transglutaminase 2", Chem. Biol., Jan. 28, 2011, pp. 58-66, vol. 18, Issue 1, Elsevier Inc., Amsterdam, Netherlands.
Dafik et al., "Activation and Inhibition of Transglutaminase 2 in Mice", PLoS One, Feb. 2, 2012, pp. 1-7, vol. 7, Issue 2, e30642, PLoS One, San Francisco, CA.
Diraimondo et al., 2013 ACS Chem. Biol.
Killackey et al., "A new class of mechanism-based inhibitors of transglutaminase enzymes inhibits the formation of cross-linked envelopes by human malignant keratinocytes", Mol Pharmacol., Feb. 15, 1989, pp. 701-706, (35), ASPET, Bethesda, MD.
Watts et al., "Structure-Activity Relationship Analysis of the Selective Inhibition of Transglutaminase 2 by Dihydroisoxazoles", J. Med. Chem., Jul. 17, 2006, pp. 7493-7501, 49(25), American Chemical Society, Washington, D.C.

* cited by examiner

*Primary Examiner* — D Margaret M Seaman
(74) *Attorney, Agent, or Firm* — Pamela J. Sherwood; Bozicevic, Field & Francis LLP

(57) ABSTRACT

Compositions and methods are provided for modulating the physiological activation of tissue transglutaminase (TG2); which methods can include inhibiting the activity of TG2 associated with inflammatory disorders, which disorders may include, without limitation, sepsis, ischemic reperfusion injury, renal fibrosis, and the like.

12 Claims, 4 Drawing Sheets

X is a (rigid) spacer between R and the proline ring, e.g. but not limited to:

a)   d)

b)   e)

c)   f)

(where Y, $Y_1$, $Y_2$ may be H or small alkyl)

R is a hydrophobic / aliphatic / aromatic / heteroaromatic moiety,
e.g. but not limited to:

(where Y may be H, a halogen, OH, OR, or other substituents

A) Liver

B) Lung

C) Small Intestine

D) Quantification

MODULATION OF TISSUE TRANSGLUTAMINASE ACTIVATION IN DISEASE

CROSS-REFERENCE TO RELATED APPLICATIONS

This application claims the benefit of PCT patent application no. PCT/US2015/013576 entitled "MODULATION OF TISSUE TRANSGLUTAMINASE ACTIVATION IN DISEASE" filed on Jan. 29, 2015 and U.S. provisional patent application No. 61/933,711 entitled "MODULATION OF TISSUE TRANSGLUTAMINASE ACTIVATION IN DISEASE" filed on Jan. 30, 2014, which are herein incorporated by reference in their entirety.

GOVERNMENT RIGHTS

This invention was made with Government support under contract DK063158 awarded by the National Institutes of Health. The Government has certain rights in the invention.

BACKGROUND OF THE INVENTION

Transglutaminase 2 (TG2) is a member of the human transglutaminase family of enzymes, which is abundantly expressed in various tissues and is found in both intra- and extracellular locations (Lorand and Graham, 2003 Nat. Rev. Mol. Biol. 4, 140-156). It possesses the catalytic activity of crosslinking of glutamine sidechains on substrate peptides or proteins with biogenic small molecule or protein-bound amines, which is subject to elaborate posttranslational regulation. TG2 has been attributed with various biological functions (for reviews, see e.g. (Iismaa et al., 2009 Physiol. Rev. 89, 991-1023; Mehta et al., 2005; Nurminskaya and Belkin, 2012 Int. Rev. Cell Mol. Biol. 294, 1-97) and it has been implicated in the pathogenesis of a broad range of human diseases, particularly inflammatory disorders.

Examples of such disorders are sepsis, where studies on TG2$^{-/-}$ mice suggest a pathogenic role for TG2 in the development of endotoxic shock (Falasca et al., 2008 J. Immunol. 180, 2616-2624). Similarly, the crosslinking activity of TG2 has been implicated in the development of vascular calcification and renal fibrosis (Chen et al., 2013 Am. J. Nephrol. 37, 191-198). Additionally, it might play a pathogenic role in ischemic reperfusion injury, as suggested by studies involving genetic ablation or pharmacologic inhibition of TG2 (Kim et al., 2010 Biochem. Biophys. Res. Commun. 403, 479-484; Shin et al., 2008 Biochem. Biophys. Res. Commun. 365, 509-514)

Such reports have motivated the development of TG2 inhibitors as tools for TG2 research. One such class of compounds is based on the mildly electrophilic 3-bromo-4,5-dihydroisoxazole (DHI) moiety. Early studies in the literature (Castelhano et al., 1988 Biochem. Biophys. Res. Commun. 365, 509-514; Killackey et al., 1989 Mol Pharmacol. 35, 701-706) and previous studies from our lab (Choi et al., 2005 Chem. Biol. 12, 469-475; Watts et al., 2006 J. Med. Chem. 49, 7493-7501) have resulted in the discovery of ERW1041E, a moderately potent inhibitor of TG2, which has found utility as a tool compound to study TG2 biology. As such, it has been shown that this inhibitor is capable of blocking the catalytic activity of TG2 in cell culture (Dafik and Khosla, 2011 Chem. Biol. 18, 58-66), in poly-I:C induced intestinal injury in mice (Dafik et al., 2012 PLoS One 7, e30642) and in the hypoxia-induced model of murine pulmonary hypertension (Diraimondo et al., 2013 ACS Chem. Biol.) In the latter study, it was also demonstrated that the inhibitor is well tolerated during twice daily administration for several weeks.

These studies showed the promise of DHI-based inhibitors in vivo, however there are several drawbacks of ERW1041E that needed to be addressed in a clinical lead compound, namely its moderate potency and its lack of selectivity. A higher potency would allow a reduction in the dose of the TG2 inhibitor and thus reduce the chance of off-target effects. Regarding its selectivity, a clinical lead compound would need to be selective for TG2 versus catalytically active transglutaminases in humans. Crossreactivity of a clinical lead with the epidermal transglutaminase 1 (TG1) and the fibrin-stabilizing Factor XIIIa (FXIIIa) would be particularly undesirable, given that loss-of-function mutations in either genes give rise to stark disease-phenotypes in humans (see e.g. Klöck et al., 2012 Semin. Immunopathol. 34, 513-522). The present invention addresses the need for improved, clinically useful compounds.

SUMMARY OF THE INVENTION

Compositions and methods are provided for the selective inhibition of TG2, e.g. as a therapeutic agent for treatment of inflammatory conditions, e.g. sepsis, ischemic reperfusion injuries, fibrosis, etc. TG2 inhibitors of the invention have a structure as set forth as Formula I herein. Compositions include a TG2 inhibitor of the invention and a pharmaceutically acceptable excipient. Such compositions can be provided in a unit dose formulation, e.g. comprising a dose of TG2 inhibitor effective in inhibiting TG2 activity, reducing inflammation, etc. Compositions optionally include a second pharmaceutically active agent, including without limitation, natural or engineered forms of mammalian thioredoxin. In some embodiments a pharmaceutical formulation is suitable for systemic administration, e.g. parenteral administration. In some embodiments the TG2 inhibitor is (2S,4R)-quinolin-3-ylmethyl 2-((((S)-3-bromo-4,5-dihydroisoxazol-5-yl)methyl)carbamoyl)-4-(nicotinamido)pyrrolidine-1-carboxylate.

In the methods of the invention, an effective dose of a TG2 inhibitor of the invention is administered to an individual having undesirable TG2 activity, which activity may, without limitation, be associated with an inflammatory condition. An effective dose may be sufficient to significantly reduce the titer of circulating proinflammatory cytokines, including without limitation one or more of IL-6, PAI-1 and MIP1α. In some embodiments the inflammatory condition is sepsis, ischemic reperfusion injuries, fibrosis, celiac sprue, etc.

The TG2 inhibitor may be concomitantly administered with an effective dose of mammalian thioredoxin, where the combined therapy of TG2 inhibitor and thioredoxin provide for an enhanced or synergistic effectiveness compared to administration of either agent as a monotherapy. Suitable thioredoxin proteins are obtained from a variety of sources, including without limitation human thioredoxin and engineered long-acting derivatives (e.g., Tanaka et al., J. Pharmacol. Exp. Ther. 345, 271-283, 2013).

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE EMBODIMENTS

Definitions

Figure 1:
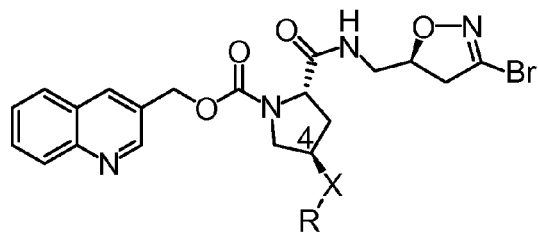
FIG. 1: General structure of potent and selective TG2 inhibitors. To gain potency and selectivity, a substituent (R) is introduced in the trans-position of L-proline in the inhibitor core. (R) is attached to the proline ring in a rigid fashion, using linkers (X). Desirable examples for the identity of (R) include substituted or unsubstituted aromatic or heteroaromatic moieties. A direct attachment (mode a, furnishing 4-aryl-prolines) or through an amide linkage (mode b, furnishing 4-arylamido-prolines) are also desirable examples for (X). Inversing the sense of the amide bond or using E/Z olefins or alkynes (modes c-f) fulfill the same function.
Figure 1:
Figure 1:
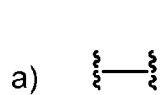
Figure 1:
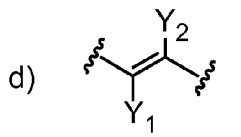
Figure 1:
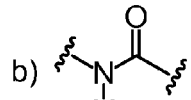
Figure 1:
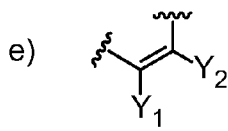
Figure 1:
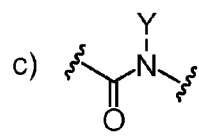
Figure 1:
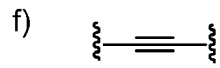
Figure 1:
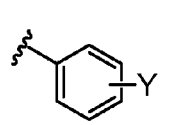
Figure 1:
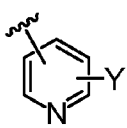
Figure 1:
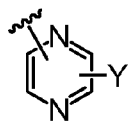
Figure 1:
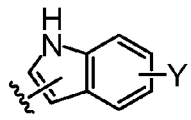

As used herein, the term "therapeutic drug" or "therapeutic regimen" refers to an agent used in the treatment or prevention of a disease or condition, particularly an inflammatory condition for the purposes of the present invention. Of interest are therapeutic treatment methods, clinical trials using such therapies, screening assays for such therapies, and monitoring of patients undergoing such therapy.

In some embodiments, the therapy involves treatment of an individual, e.g. an individual suffering from an inflammatory condition, with an agent of the invention. Patients may be control patients that have not been treated, or patients subject to a clinical regimen of interest. A "patient," or individual, as used herein, describes an organism, including mammals, particularly humans.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The term "pharmacokinetics," refers to the mathematical characterization of interactions between normal physiological processes and a therapeutic drug over time (i.e., body effect on drug). Certain physiological processes (absorption, distribution, metabolism, and elimination) will affect the ability of a drug to provide a desired therapeutic effect in a patient. Knowledge of a drug's pharmacokinetics aids in interpreting drug blood stream concentration and is useful in determining pharmacologically effective drug dosages.

The term "in combination with", or "concomitantly" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

The term "isolated compound" means a compound which has been substantially separated from, or enriched relative to, other compounds with which it occurs in nature or during chemical synthesis. Isolated compounds are usually at least about 80% pure, or at least about 90% pure, at least about 98% pure, or at least about 99% pure, by weight. The present invention is meant to encompass diastereomers as well as their racemic and resolved, enantiomerically pure forms and pharmaceutically acceptable salts thereof.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is preferably sterile, and free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Compounds included in the present compositions that are acidic in nature may react with any number of inorganic and organic bases to form pharmaceutically acceptable base salts. Bases may include, for example, the mineral bases, such as NaOH and KOH, but one of skill in the art would appreciate that other bases may also be used. See Ando et al., Remington: The Science and Practice of Pharmacy, 20th ed. 700-720 (Alfonso R. Gennaro ed.), 2000.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

In some embodiments, the pharmaceutically acceptable addition salts of the compounds described herein may also exist as various solvates, such as, for example, with water, methanol, ethanol, dimethylformamide, and the like. Mixtures of such solvates may also be prepared. The source of such solvate may be from the solvent of crystallization, inherent in the solvent of preparation or crystallization, or adventitious to such solvent.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

The terms "contact", "contacts", "contacting" have their normal meaning and refer to combining two or more entities (e.g., two proteins, a polynucleotide and a cell, a cell and a candidate agent, etc.) Contacting can occur in vitro, in situ or in vivo and is used interchangeably with "expose to", "exposed to", "exposing to."

As used herein, the terms "reduce", "decrease" and "inhibit" are used together because it is recognized that, in some cases, an observed activity can be reduced below the level of detection of a particular assay. As such, it may not always be clear whether the activity is "reduced" or "decreased" below a level of detection of an assay, or is completely "inhibited".

As used herein, compounds which are "commercially available" may be obtained from standard commercial sources including Acros Organics (Geel Belgium), Aldrich Chemical (Milwaukee Wis., including Sigma Chemical and Fluke), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.); Molecular Probes (Eugene, Oreg.); Invitrogen (Carlsbad, Calif.), Applied Biosystems, Inc. (Foster City, Calif.), Glen Research (Sterling, Va.), Biosearch Technologies (Novato, Calif.), Anaspec (Fremont, Calif.), Berry & Associates (Dexter, Mich.) and Chem-Impex International Inc. (Wood Dale, Ill.)

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified through various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. The term lower alkyl will be used herein as known in the art to refer to an alkyl, straight, branched or cyclic, of from about 1 to 6 carbons. It will be understood by those skilled in the art, with respect to any group containing one or more substituents, that such groups are not intended to introduce any substitution or substitution patterns that are sterically impractical, synthetically non-feasible and/or inherently unstable.

When describing the compounds, pharmaceutical compositions containing such compounds and methods of using such compounds and compositions, the following terms have the following meanings unless otherwise indicated. It should also be understood that any of the moieties defined forth below may be unsubstituted or substituted with a variety of substituents, and that the respective definitions are intended to include both unsubstituted and substituted moieties within their scope.

"Acyl" refers to a —C(O)R group, where R is hydrogen, alkyl, alkenyl, cycloalkyl, heterocycloalkyl, aryl, arylalkyl, heteroalkyl, heteroalkenyl, or heteroaryl as defined herein. Representative examples include, but are not limited to, formyl, acetyl, cyclohexylcarbonyl, cyclohexylmethylcarbonyl, benzoyl, benzylcarbonyl and the like.

"Acylamino" refers to a —NR'C(O)R group, where R' is hydrogen, alkyl, cycloalkyl, heterocycloalkyl, aryl, arylalkyl, heteroalkyl, heteroaryl, heteroarylalkyl and R is hydrogen, alkyl, alkoxy, cycloalkyl, heterocycloalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)H, —OC(O)-alkyl, —OC(O)-aryl or —OC(O)-cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkynyl and alkynylene. Lower aliphatic groups typically have from 1 or 2 to 6 or 12 carbon atoms.

"Alkenyl" refers to monovalent olefinically unsaturated hydrocarbyl groups having up to about 11 carbon atoms, such as from 2 to 8 carbon atoms, and including from 2 to 6 carbon atoms, which can be straight-chained or branched and having at least 1 and including from 1 to 2 sites of olefinic unsaturation. Particular alkenyl groups include ethenyl (—CH=CH2), n-propenyl (—CH2CH=CH2), isopropenyl (—C(CH3)=CH2), vinyl and substituted vinyl, and the like.

"Alkoxy" refers to the group —O-alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical —C(O)-alkoxy where alkoxy is as defined herein.

"Alkoxycarbonylamino" refers to the group —NRC(O) OR' where R is hydrogen, alkyl, aryl or cycloalkyl, and R' is alkyl or cycloalkyl.

"Alkyl" refers to monovalent saturated aliphatic hydrocarbyl groups particularly having up to about 12 or 18 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, isobutyl, tert-butyl, n-hexyl, n-octyl, tert-octyl and the like. The term "alkyl" also includes "cycloalkyls" as defined herein.

"Alkylene" refers to divalent saturated aliphatic hydrocarbyl groups particularly having up to about 12 or 18 carbon atoms and more particularly 1 to 6 carbon atoms which can be straight-chained or branched. This term is exemplified by groups such as methylene (—CH2-), ethylene (—CH2CH2-), the propylene isomers (e.g., —CH2CH2CH2- and —CH(CH3)CH2-) and the like.

"Alkynyl" refers to acetylenically unsaturated hydrocarbyl groups particularly having up to about 12 or 18 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH2C≡CH), and the like.

"Amino" refers to the radical —NH2.

"Aminocarbonyl" refers to the group —C(O)NRR where each R is independently hydrogen, alkyl, aryl or cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalky, or where the R groups are joined to form an alkylene group.

"Aralkyl" or "arylalkyl" refers to an alkyl group, as defined above, substituted with one or more aryl groups, as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some cases, an aryl group includes from 6 to 14 carbon atoms.

"Aryloxy" refers to —O-aryl groups wherein "aryl" is as defined herein.

"Azido" refers to a —N3 group.

"Carbonyl" refers to —C(O)— groups, for example, a carboxy, an amido, an ester, a ketone, or an acyl substituent.

"Carboxyl" refers to a —C(O)OH group

"Cyano" refers to a —CN group.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Heterocycloalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl.

"Halogen" or "halo" refers to fluoro, chloro, bromo and iodo.

"Hetero" when used to describe a compound or a group present on a compound means that one or more carbon atoms in the compound or group have been replaced by, for example, a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, e.g., heterocycloalkenyl, cycloheteroalkenyl, e.g., heterocycloheteroalkenyl and the like having from 1 to 5, and particularly from 1 to 3 heteroatoms. A heteroatom is any atom other than carbon or hydrogen and is typically, but not exclusively, nitrogen, oxygen, sulfur, phosphorus, boron, chlorine, bromine, or iodine.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. The heteroaryl group can be a 5-20 membered heteroaryl, or 5-10 membered heteroaryl. Particular heteroaryl groups are those derived from thiophen, pyrrole, benzothiophene, benzofuran, indole, pyridine, quinoline, imidazole, oxazole and pyrazine.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings include from one to three halo, trihalomethyl, amino, protected amino, amino salts, mono-substituted amino, di-substituted amino, carboxy, protected carboxy, carbon/late salts, hydroxy, protected hydroxy, salts of a hydroxy group, lower alkoxy, lower alkylthio, alkyl, substituted alkyl, cycloalkyl, substituted cycloalkyl, (cycloalkyl) alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a C1 to C4 alkoxy group, similarly, "lower alkylthio" means a C1 to C4 alkylthio group.

"Heterocycle" refers to organic compounds that contain a ring structure containing atoms in addition to carbon, such as sulfur, oxygen or nitrogen, as part of the ring. They may be either simple aromatic rings or non-aromatic rings. Examples include azoles, morpholine, piperazine, pyridine, pyrimidine and dioxane. The maximum number of heteroatoms in a stable, chemically feasible heterocyclic ring, whether it is aromatic or non-aromatic, is determined by factors such as, the size of the ring, the degree of unsaturation and the valence of the heteroatoms. In general, a heterocyclic ring may have one to four heteroatoms so long as the heteroaromatic ring is chemically feasible and stable.

"Hydroxyl" refers to a —OH group.

"Stereoisomer" as it relates to a given compound refers to another compound having the same molecular formula, wherein the atoms making up the other compound differ in the way they are oriented in space, but wherein the atoms in the other compound are like the atoms in the given compound with respect to which atoms are joined to which other atoms (e.g. an enantiomer, a diastereomer, or a geometric isomer). See for example, Morrison and Boyd, Organic Chemistry, 1983, 4th ed., Allyn and Bacon, Inc., Boston, Mass., p. 123.

"Substituted" refers to a group in which one or more hydrogen atoms are each independently replaced with the same or different substituent(s). "Substituted" groups particularly refer to groups having 1 or more substituents, for instance from 1 to 5 substituents, and particularly from 1 to 3 substituents, selected from the group consisting of acyl, acylamino, acyloxy, alkoxy, alkoxycarbonyl, alkoxycarbonylamino, amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, thioaryloxy, thioketo, thiol, alkyl-S(O)—, aryl-S(O)—, alkyl-S(O)$_2$— and aryl-S(O)$_2$. Substituents of interest may include, but are not limited to, —X, —R8 (with the proviso that R8 is not hydrogen), —O—, =O, —OR8, —SR8, —S—, =S, —NR8R9, =NR8, —CX3, —CF3, —CN, —OCN, —SCN, —NO, —NO2, =N2, —N3, —S(O)2O—, —S(O)2OH, —S(O)2R8, —OS(O2)O—, —OS(O)2R8, —P(O)(O—)2, —P(O)(OR8)(O—), —OP(O)(OR8)(OR9), —C(O)R8, —C(S)R8, —C(O)OR8, —C(O)NR8R9, —C(O)O—, —C(S)OR8, —NR10C(O)NR8R9, vNR10C(S)NR8R9, —NR11C(NR10)NR8R9 and —C(NR10)NR8R9, where each X is independently a halogen and R8 is an alkyl, an alkenyl, an alkynyl, a heterocycle or an aryl.

"Sulfonyl" refers to the group —SO2-. Sulfonyl includes, for example, methyl-SO2-, phenyl-SO2-, and alkylamino-SO2-.

"Sulfinyl" refers to the group —S(O)—.

"Thioalkoxy" refers to the group —S-alkyl.

"Thioaryloxy" refers to the group —S-aryl.

"Thioketo" refers to the group =S.

"Thiol" refers to the group —SH.

"Thio" refers to the group —S—. Thio includes, for example, thioalkoxy, thioaryloxy, thioketo and thiol.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

Thioredoxin (TXN) is a 12-kD oxidoreductase enzyme containing a dithiol-disulfide active site. It is ubiquitous and found in many organisms from plants and bacteria to mammals. Multiple in vitro substrates for thioredoxin have been identified, including ribonuclease, choriogonadotropins, coagulation factors, glucocorticoid receptor, and insulin. Thioredoxins are characterized at the level of their amino acid sequence by the presence of two vicinal cysteines in a CXXC motif, e.g. trp-cys-gly-pro-cys (amino acids 30 to 34). These two cysteines are the key to the ability of thioredoxin to reduce other proteins. Thioredoxin proteins also have a characteristic tertiary structure termed the thioredoxin fold.

Various thioredoxin proteins can be administered for the purposes of the invention. In one embodiment a human protein is used, e.g. a protein based on the reference sequence Genbank NM_003329.3 or NM_001244938.1, however other TXN proteins find use, e.g. mammalian including mouse, rat, non-human primate, etc.; avian; microbial, plant, etc. By fusing thioredoxin to a serum protein such as albumin, its half-life can be significantly prolonged (e.g., Tanaka et al., J. Pharmacol. Exp. Ther. 345, 271-283, 2013).

Depending on the patient and condition being treated and on the administration route, an effective dose of thioredoxin can vary as a function of the specific inhibitor being coadministered, the severity of the symptoms, and the susceptibility of the subject to side effects. Preferred dosages for are readily determinable by those of skill in the art by a variety of means. Thioredoxin doses may include, for example, dosages of from about 0.01 mg/kg body weight, 0.05 mg/kg, 0.1 mg/kg, 0.5 mg/kg, 1 mg/kg, 5 mg/kg, 10 mg/kg, 50 mg/kg, 100 mg/kg, to about 500 mg V/kg body weight per day, e.g. about 0.5, about 1, about 5, about 10, about 50 mg/kg for an average person. Dosages are appropriately adjusted for pediatric formulation. Those of skill will readily appreciate that dose levels Compositions and Methods of Use Provided herein are therapeutic compounds that can be used to inhibit the activity of TG2. These compounds can be incorporated into a variety of formulations for therapeutic administration by a variety of routes. More particularly, the compounds disclosed herein can be formulated into pharmaceutical compositions by combination with appropriate, pharmaceutically acceptable carriers, diluents, excipients and/or adjuvants. The following are examples of compounds of the invention.

In one embodiment, a compound of the invention has the structure:

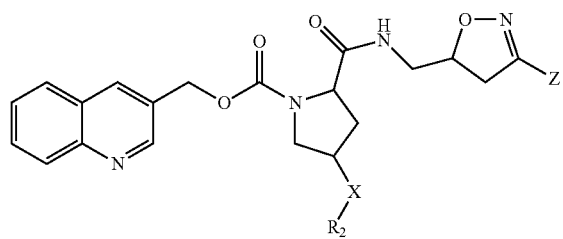

wherein Z is halogen; X is a bond, —C(O)NH—, NHC(O)—, C(O)O—, O—C(O)—, O, $CH_2$, S, NH, or $NCH_3$; and $R_2$ is optionally substituted aryl or optionally substituted heteroaryl. In one embodiment, Z is Br, F, or Cl. In another embodiment, Z is Br.

In another embodiment, a compound of the invention has a structure:

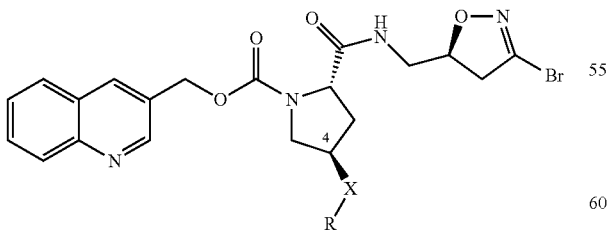

I wherein:

X is absent, or when present is a rigid spacer; and

R is a substituted or unsubstituted aromatic or heteroaromatic moiety.

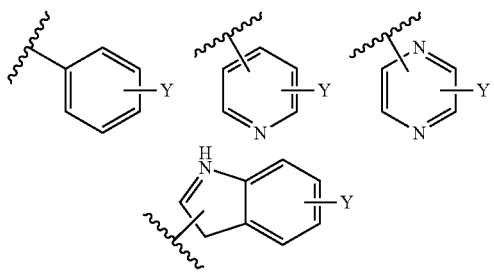

wherein Y is H, a halogen, OH, $OR^1$, or other substituents. In some embodiments $R^1$ is $C_1$-$C_6$alkyl. In yet a further embodiment, $R^1$ is selected from methyl, ethyl, n-propyl, iso-propyl. In yet a further embodiment, $R^1$ is n-butyl, iso-butyl, or tert-butyl. In one embodiment, $R^1$ is $C_3$-$C_8$cycloalkyl. In another embodiment $R^1$ is cyclopropyl, cyclobutyl, cyclopentyl, or cyclohexyl. In yet another embodiment, R is mono-substituted. In a further embodiment, R is di-substituted. In yet a further embodiment, R is tri-substituted.

In some embodiments, X is selected from:

a)

b)

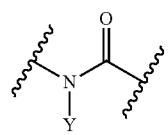

c)

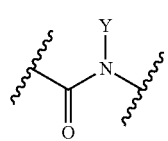

d)

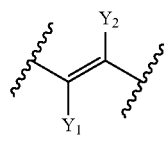

e)

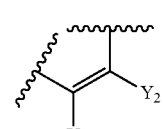

f)

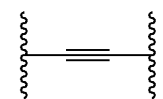

(where Y, $Y_1$, $Y_2$ may be H or small alkyl)

In some embodiments, compounds of the invention have a structure set forth in Formula II:

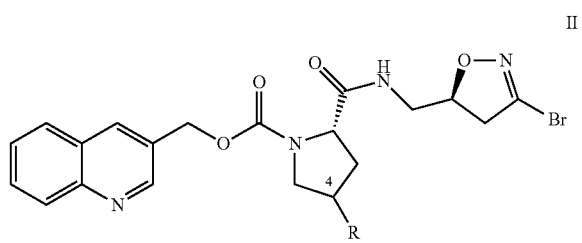

wherein R is a substituted or unsubstituted aromatic or heteroaromatic moiety or as defined above.

Desirable examples for the identity of (R) include A direct attachment (mode a, furnishing 4-aryl-prolines) or through an amide linkage (mode b, furnishing 4-arylamido-prolines) are also desirable examples for (X). Inversing the sense of the amide bond or using E/Z olefins or alkynes (modes c-f) fulfill the same function.

In another embodiment a compound of the invention has the structure:

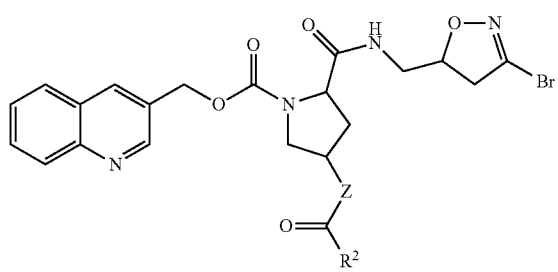

wherein Z is O or NH or $NCH_3$; and $R^2$ is optionally substituted aryl or optionally substituted heteroaryl. In one embodiment, $R^2$ aryl. In a further embodiment, aryl is phenyl. In one embodiment, heteroaryl is selected from furan, imidazole, indazole, indole, indoline, indolizine, isobenzofuran, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and xanthene. In another embodiment, the heteroaryl is pyrazine. In a further embodiment, the heteroaryl is pyridine. In yet another embodiment, aryl or heteroaryl is substituted with R. In another embodiment, R is halogen, $OR^1$, CN, $C_1$-$C_6$alkyl; and $R^1$ is H, $C_1$-$C_6$alkyl, or $C_3$-$C_8$cycloalkyl. In another embodiment halogen is Cl, Br, I or F. In a further embodiment, halogen is Cl. In another embodiment, halogen is F. In yet another embodiment the halogen is at the ortho-position. In one embodiment, the halogen is at the para-position. In a further embodiment, R is $OR^1$ where $R^1$ is H. In yet another embodiment, $R^1$ is $C_1$-$C_6$alkyl. In yet a further embodiment, $R^1$ is selected from methyl, ethyl, n-propyl, iso-propyl. In yet a further embodiment, $R^1$ is n-butyl, iso-butyl, or tert-butyl. In one embodiment, $R^1$ is $C_3$-$C_8$cycloalkyl. In another embodiment $R^1$ is cyclopropyl, cyclobutyl, cyclopentyl, or cyclohexyl.

In one embodiment, a compound of the invention has the structure:

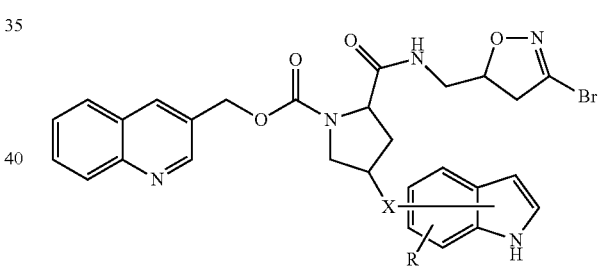

wherein R is halogen, $OR^1$, CN, $C_1$-$C_6$alkyl; and $R^1$ is H, $C_1$-$C_6$alkyl, or $C_3$-$C_8$cycloalkyl.

In another embodiment halogen is Cl, Br, I or F. In a further embodiment, halogen is Cl. In another embodiment, halogen is F. In yet another embodiment the halogen is at the ortho-position. In one embodiment, the halogen is at the para-position. In a further embodiment, R is $OR^1$ where $R^1$ is H. In yet another embodiment, $R^1$ is $C_1$-$C_6$alkyl. In yet a further embodiment, $R^1$ is selected from methyl, ethyl, n-propyl, iso-propyl. In yet a further embodiment, $R^1$ is n-butyl, iso-butyl, or tert-butyl. In one embodiment, $R^1$ is $C_3$-$C_8$cycloalkyl. In another embodiment $R^1$ is cyclopropyl, cyclobutyl, cyclopentyl, or cyclohexyl. In yet another embodiment, R is mono-substituted. In a further embodiment, R is di-substituted. In yet a further embodiment, R is tri-substituted.

In another embodiment, a compound of the invention has the structure:

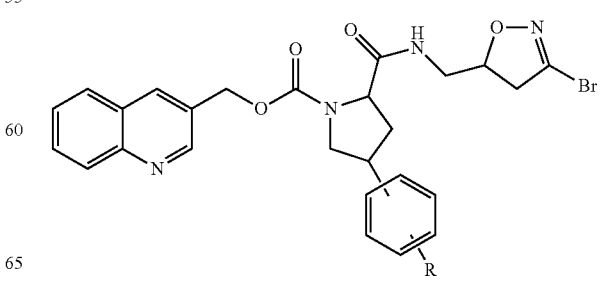

wherein X is a bond; and R is halogen, $OR^1$, CN, $C_1$-$C_6$alkyl; and $R^1$ is H, $C_1$-$C_6$alkyl, or $C_3$-$C_8$cycloalkyl. In a further embodiment, R is halogen. In yet another embodiment, halogen is F.

In one embodiment a compound of the invention has the structure:

wherein R is halogen, OR$^1$, CN, C$_1$-C$_6$alkyl; and R$^1$ is H, C$_1$-C$_6$alkyl, or C$_3$-C$_8$cycloalkyl. In another embodiment halogen is Cl, Br, I or F. In a further embodiment, halogen is Cl. In another embodiment, halogen is F. In yet another embodiment the halogen is at the ortho-position. In one embodiment, the halogen is at the para-position. In a further embodiment, R is OR$^1$ where R$^1$ is H. In yet another embodiment, R$^1$ is C$_1$-C$_6$alkyl. In yet a further embodiment, R$^1$ is selected from methyl, ethyl, n-propyl, iso-propyl. In yet a further embodiment, R$^1$ is n-butyl, iso-butyl, or tert-butyl. In one embodiment, R$^1$ is C$_3$-C$_8$cycloalkyl. In another embodiment R$^1$ is cyclopropyl, cyclobutyl, cyclopentyl, or cyclohexyl. In yet another embodiment, R is mono-substituted. In a further embodiment, R is di-substituted. In yet a further embodiment, R is tri-substituted.

In some embodiments the TG2 inhibitor is one or more of (2S,4R)-quinolin-3-ylmethyl 4-benzamido-2-((((S)-3-bromo-4,5-dihydroisoxazol-5-yl)methyl)carbamoyl)pyrrolidine-1-carboxylate; (2S,4R)-quinolin-3-ylmethyl 2-((((S)-3-bromo-4,5-dihydroisoxazol-5-yl)methyl) carbamoyl)-4-(2-hydroxybenzamido)pyrrolidine-1-carboxylate; (2S,4R)-quinolin-3-ylmethyl 2-((((S)-3-bromo-4,5-dihydroisoxazol-5-yl)methyl) carbamoyl)-4-(3-hydroxybenzamido) pyrrolidine-1-carboxylate; (2S,4R)-quinolin-3-ylmethyl 2-((((S)-3-bromo-4,5-dihydroisoxazol-5-yl)methyl) carbamoyl)-4-(4-hydroxybenzamido)pyrrolidine-1-carboxylate; (2S,4R)-quinolin-3-ylmethyl 2-((((S)-3-bromo-4,5-dihydroisoxazol-5-yl)methyl)carbamoyl)-4-(nicotinamido) pyrrolidine-1-carboxylate; (2S,4R)-quinolin-3-ylmethyl 2-((((S)-3-bromo-4,5-dihydroisoxazol-5-yl)methyl) carbamoyl)-4-(pyrazine-2-carboxamido)pyrrolidine-1-carboxylate; 1-(((3R,5S)-5-((((S)-3-bromo-4,5-dihydroisoxazol-5-yl)methyl)carbamoyl)-1-((quinolin-3-ylmethoxy) carbonyl)pyrrolidin-3-yl)carbamoyl) cyclobutanecarboxylic acid; (2S,4S)-quinolin-3-ylmethyl 2-((((S)-3-bromo-4,5-dihydroisoxazol-5-yl)methyl)carbamoyl)-4-phenylpyrrolidine-1-carboxylate; (2S,4R)-quinolin-3-ylmethyl 2-((((S)-3-bromo-4,5-dihydroisoxazol-5-yl)methyl)carbamoyl)-4-phenylpyrrolidine-1-carboxylate; (2S,4S)-quinolin-3-ylmethyl 2-((((S)-3-bromo-4,5-dihydroisoxazol-5-yl) methyl)carbamoyl)-4-(2-hydroxyphenyl)pyrrolidine-1-carboxylate; (2S,4S)-quinolin-3-ylmethyl 2-((((S)-3-bromo-4,5-dihydroisoxazol-5-yl)methyl) carbamoyl)-4-(3-hydroxyphenyl)pyrrolidine-1-carboxylate; (2S,4S)-quinolin-3-ylmethyl 2-((((S)-3-bromo-4,5-dihydroisoxazol-5-yl)methyl) carbamoyl)-4-(4-hydroxyphenyl)pyrrolidine-1-carboxylate; (2S,4S)-quinolin-3-ylmethyl 2-((((S)-3-bromo-4,5-dihydroisoxazol-5-yl)methyl) carbamoyl)-4-(3-chlorophenyl)pyrrolidine-1-carboxylate; (2S,4S)-quinolin-3-ylmethyl 2-((((S)-3-bromo-4,5-dihydroisoxazol-5-yl) methyl) carbamoyl)-4-(4-chlorophenyl)pyrrolidine-1-carboxylate; (2S,4S)-quinolin-3-ylmethyl 2-((((S)-3-bromo-4,5-dihydroisoxazol-5-yl)methyl)carbamoyl)-4-(5-fluoro-1H-indol-3-yl)pyrrolidine-1-carboxylate; (S)-quinolin-3-ylmethyl 2-((((S)-3-bromo-4,5-dihydroisoxazol-5-yl) methyl) carbamoyl)-4-phenyl-2,5-dihydro-1H-pyrrole-1-carboxylate.

In some embodiments the TG2 inhibitor is (2S,4R)-quinolin-3-ylmethyl 2-((((S)-3-bromo-4,5-dihydroisoxazol-5-yl)methyl)carbamoyl)-4-(nicotinamido)pyrrolidine-1-carboxylate.

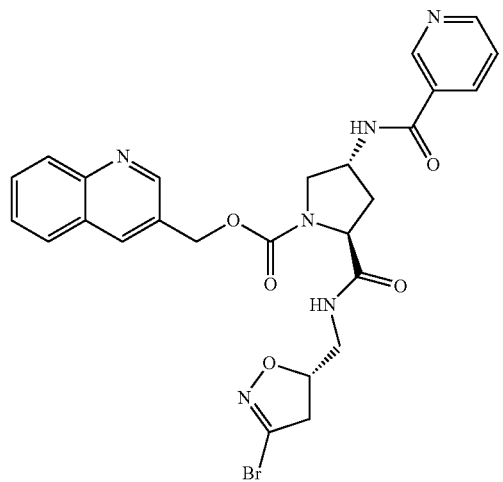 [SMILES: O=C(N[C@@H]1C[C@@H](C(=O)NC[C@@H]2CC(Br)=NO2)N(C(=O)OCc2cnc3ccccc3c2)C1)c1cccnc1]

In certain embodiments, the subject compounds include a substituent that contributes to optical isomerism and/or stereo isomerism of a compound. Salts, solvates, hydrates, and prodrug forms of a compound are also of interest. All such forms are embraced by the present invention. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Agents that inhibit TG2 are administered to an individual in need thereof, at a dose and for a period of time effective to achieve the desired result. The present invention provides the inhibitors in a variety of formulations for therapeutic administration. In one aspect, the agents are formulated into pharmaceutical compositions by combination with appropriate, pharmaceutically acceptable carriers or diluents, and are formulated into preparations in solid, semi-solid, liquid or gaseous forms, such as tablets, capsules, powders, granules, ointments, solutions, suppositories, injections, inhalants, gels, microspheres, and aerosols. As such, administration of the inhibitors is achieved in various ways, although oral administration is a preferred route of administration. In some formulations, the inhibitor is localized by virtue of the formulation, such as the use of an implant that acts to retain the active dose at the site of implantation, or is otherwise localized by virtue of the relevant pharmacokinetics.

In some pharmaceutical dosage forms, the inhibitors are administered in the form of their pharmaceutically acceptable salts. In some dosage forms, the inhibitor is used alone, while in others, it is administered in combination with another pharmaceutically active compounds, including without limitation thioredoxin. The second pharmaceutical agent, e.g. thioredoxin, can be co-formulated with the TG2 inhibitor, or can be separately formulated but administered concomitantly.

Formulations are typically provided in a unit dosage form, where the term "unit dosage form," refers to physically discrete units suitable as unitary dosages for human subjects, each unit containing a predetermined quantity of inhibitor calculated in an amount sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutical compositions according to the present invention comprise at least one compound according to the present invention as an active ingredient together with at least one pharmaceutically acceptable (i.e. non-toxic) carrier, excipient and/or diluent. The pharmaceutical compositions of the present invention can be prepared in a conventional solid or liquid carrier or diluent and a conventional pharmaceutically made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutaneous, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention and/or a pharmaceutical acceptable salt thereof as active ingredient.

The pharmaceutical compositions according to the present invention containing at least one compound according to the present invention and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule. Powders and tablets may contain about 5 to about 95-weight % of the derivatives according to the general formula (I) or analogues compound thereof or the respective pharmaceutically active salt as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimize the therapeutic effect(s), e.g. anti-cancer activity or activity against cancer metastases and the like. Suitable dosage forms for sustained release include tablets having layers of varying disintegration rates or controlled release, polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration.

Aerosol preparations suitable for inhalation may include solutions and solids in powder form, which may be present in combination with a pharmaceutically acceptable carrier such as an inert, compressed gas, e.g. nitrogen.

For preparing suppositories, a low melting wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methylcellulose, polyvinyl alcohols, or denatured gelatins or starch for holding or containing compositions comprising the active ingredient(s). Capsules with hard shells are typically made of blended of relatively high gel strength gelatins from bones or pork skin. The capsule itself may contain small amounts of dyes, opaquing agents, plasticisers and/or preservatives.

Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn, rice, and potato, and celluloses such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscarmellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat, corn, rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances which are added to the dosage form to enable the tablet granules etc. after being compressed to release from the mould by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

The compounds of the present invention are suitable for use in medicine, particularly in human medicine, but also in veterinary medicine. The dosage of the compounds may be determined by a skilled practitioner according to the type and severity of the disorder to be treated.

Depending on the patient and condition being treated and on the administration route, the inhibitor is administered in dosages of from about 0.01 mg/kg body weight, 0.05 mg/kg, 0.1 mg/kg, 0.5 mg/kg, 1 mg/kg, 5 mg/kg, 10 mg/kg, 50 mg/kg, 100 mg/kg, to about 500 mg V/kg body weight per day, e.g. about 0.1, about 0.5, about 1, about 5, about 10 mg/kg for an average person. Dosages are appropriately adjusted for pediatric formulation. Those of skill will readily appreciate that dose levels can vary as a function of the specific inhibitor, the severity of the symptoms, and the susceptibility of the subject to side effects. Some of the inhibitors of the invention are more potent than others. Preferred dosages for a given inhibitor are readily determinable by those of skill in the art by a variety of means. A preferred means is to measure the physiological potency of a given compound.

The dosage of the therapeutic formulation can vary widely, depending upon the nature of the disease, the frequency of administration, the manner of administration, the clearance of the agent from the patient, and the like. The initial dose can be larger, followed by smaller maintenance doses. The dose can be administered as infrequently as weekly or biweekly, or more often fractionated into smaller doses and administered daily, with meals, semi-weekly, and the like, to maintain an effective dosage level.

Disease Conditions

Conditions of interest for methods of the present invention include a variety of inflammatory conditions. In some embodiments of the invention, a patient is diagnosed as having an inflammatory condition, for which treatment is provided.

Sepsis refers to a serious infection, localized, bacteremic or fungal, that is accompanied by systemic manifestations of inflammation. The term "onset of sepsis" refers to an early stage of sepsis, i.e. prior to a stage when the clinical manifestations are sufficient to support a clinical suspicion of sepsis. A TG2 inhibitor, alone or in combination with thioredoxin, may be administered at this stage, or upon definitive diagnosis of sepsis. "Severe sepsis" refers to sepsis associated with organ dysfunction, hypoperfusion abnormalities, or sepsis-induced hypotension. Hypoperfusion abnormalities include, but are not limited to, lactic acidosis, oliguria, or an acute alteration in mental status. "Septic shock" refers to sepsis-induced hypotension that is not responsive to adequate intravenous fluid challenge and with manifestations of peripheral hypoperfusion.

"Systemic inflammatory response syndrome", or "SIRS", refers to a clinical response to a variety of severe clinical insults, for example as manifested by two or more of the following conditions within a 24-hour period: body temperature greater than 38° C. or less than 36° C.; heart rate (HR) greater than 90 beats/minute; respiratory rate (RR) greater than 20 breaths/minute, or $P_{CO2}$ less than 32 mm Hg, or requiring mechanical ventilation; and white blood cell count (WBC) either greater than $12 \times 10^9$/L or less than $4 \times 10^9$/L or having greater than 10% immature forms (bands). SIRS may result from a variety of conditions, including trauma such as burns or other insults, including sepsis.

Reperfusion injury generally refers to tissue damage caused when blood supply returns to the tissue after a period of ischemia or lack of oxygen. The absence of oxygen and nutrients from blood during the ischemic period creates a condition in which the restoration of circulation results in inflammation and oxidative damage through the induction of oxidative stress rather than restoration of normal function. Neutrophil activity is also implicated in reperfusion injury. Biopsies of post-ischemic muscles have shown infiltration with granulocytes, mostly neutrophils, during ischemia and reperfusion and an increase in circulating neutrophils. Neutrophil activity seems to be associated with endothelial damage and is part of the inflammatory response, coordinated by a network of inflammatory cytokines and chemokines. IL-1, TNF-alpha and IL-6 all increased dramatically on reperfusion. Where large volumes of tissue are reperfused, post-ischemic syndrome may develop. This has many features in common with the systemic inflammatory response syndrome (SIRS) that occurs in sepsis, including acute respiratory distress and organ failure, and it is similarly associated with large amounts of inflammatory cytokines in circulation.

A number of different tissues can be affected by ischemic reperfusion injury. The following provides a non-limiting discussion of specific conditions where the TG2 inhibitors of the present invention can find therapeutic use by administered an effective dose of the TG2 inhibitor, preferably prior to reperfusion, although the inhibitors can also be provided following reperfusion, e.g. within about 6 hrs, within about 12 hrs., within about 18 hr., within about 24 hours, within about 48 hours, and the like.

In frost-bite, ice crystals form within or between tissue cells, essentially freezing the tissue and causing cell death. Adjacent unfrozen areas are at risk because local vasoconstriction and thrombosis can cause endothelial and ischemic damage. With reperfusion during rewarming, inflammatory cytokines are released, exacerbating tissue injury. A TG2 inhibitor of the invention, alone or in combination with thioredoxin, can be administered to reduce inflammatory damage resulting from reperfusion injury associated with frostbite.

Shock is a state of organ hypoperfusion with resultant cellular dysfunction and death. Mechanisms may involve decreased circulating volume, decreased cardiac output, and vasodilation, sometimes with shunting of blood to bypass capillary exchange beds. Symptoms include altered mental status, tachycardia, hypotension, and oliguria. Diagnosis is clinical, including BP measurement and sometimes markers of tissue hypoperfusion (eg, blood lactate, base deficit). Treatment is with fluid resuscitation, including blood products if necessary, correction of the underlying disorder, and sometimes vasopressors. The fundamental defect in shock is reduced perfusion of vital tissues. Once perfusion declines and $O_2$ delivery to cells is inadequate for aerobic metabolism, cells shift to anaerobic metabolism with increased production of $CO_2$ and accumulation of lactic acid. Cellular function declines, and if shock persists, irreversible cell damage and death occur. In septic shock, vasodilation of capacitance vessels leads to pooling of blood and hypotension because of "relative" hypovolemia (ie, too much volume to be filled by the existing amount of blood). Localized vasodilation may shunt blood past the capillary exchange beds, causing focal hypoperfusion despite normal cardiac output and BP. Additionally, excess NO is converted to peroxynitrite, a free radical that damages mitochondria and decreases ATP production. Reperfusion of ischemic cells can cause further injury. As substrate is reintroduced, neutrophil activity may increase, increasing production of damaging superoxide and hydroxyl radicals. After blood flow is restored, inflammatory mediators may be circulated to other organs. A TG2 inhibitor of the invention, alone or in combination with thioredoxin, can be administered to reduce inflammatory damage resulting from reperfusion injury associated with shock.

Ischemic stroke is sudden neurologic deficits that result from focal cerebral ischemia associated with permanent brain infarction (eg, positive results on diffusion-weighted MRI). Common causes are (from most to least common) atherothrombotic occlusion of large arteries; cerebral embolism (embolic infarction); nonthrombotic occlusion of small, deep cerebral arteries (lacunar infarction); and proximal arterial stenosis with hypotension that decreases cerebral blood flow in arterial watershed zones (hemodynamic stroke). Diagnosis is clinical, but CT or MRI is done to exclude hemorrhage and confirm the presence and extent of stroke. Thrombolytic therapy may be useful acutely in certain patients. Depending on the cause of stroke, carotid endarterectomy or stenting, antiplatelet drugs, or warfarin may help reduce risk of subsequent strokes. Mechanisms of ischemic injury include edema, microvascular thrombosis, programmed cell death (apoptosis), and infarction with cell necrosis. Inflammatory mediators (eg, IL-1B, tumor necrosis factor-α) contribute to edema and microvascular thrombosis. A TG2 inhibitor of the invention, alone or in combination with thioredoxin, can be used to reduce inflammatory damage resulting from reperfusion injury associated with ischemic stroke.

Acute coronary syndromes (ACS), including myocardial ischemia, result from acute obstruction of a coronary artery. Consequences depend on degree and location of obstruction and range from unstable angina to non-ST-segment elevation MI (NSTEMI), ST-segment elevation MI (STEMI), and sudden cardiac death. Symptoms are similar in each of these syndromes (except sudden death) and include chest discomfort with or without dyspnea, nausea, and diaphoresis. Diagnosis is by ECG and the presence or absence of serologic markers. Treatment is antiplatelet drugs, anticoagulants, nitrates, β-blockers, and, for STEMI, emergency reperfusion via fibrinolytic drugs, percutaneous intervention, or, occasionally, coronary artery bypass graft surgery. A TG2 inhibitor of the invention, alone or in combination with thioredoxin, can be administered to reduce inflammatory damage resulting from reperfusion injury associated with myocardial ischemia.

Renal fibrosis is the consequence of an excessive accumulation of extracellular matrix that occurs chronic kidney disease. The pathogenesis of renal fibrosis is a progressive process that ultimately leads to end-stage renal failure, a devastating disorder that requires dialysis or kidney transplantation. Several cellular pathways, including mesangial and fibroblast activation as well as tubular epithelial-mesenchymal transition, have been identified as the major avenues for the generation of the matrix-producing cells in diseased conditions. The pathologic findings of renal fibrosis are often described as glomerulosclerosis, tubulo-interstitial fibrosis, inflammatory infiltration, and loss of renal parenchyma characterized by tubular atrophy, capillary loss, and podocyte depletion. After the initial injury, the affected kidney tissues undergo a series of events in an attempt to repair and recover from the damage. These processes include kidney resident cell activation, which leads to the production and secretion of proinflammatory cytokines. The gradients of chemotactic cytokines provide a directional signal for guiding the infiltration of inflammatory monocytes/macrophages and T cells to the injured sites. Depending on the etiology of renal injury, glomerular or interstitial infiltrated inflammatory cells become activated, and produce injurious molecules such as reactive oxygen species, as well as fibrogenic and inflammatory cytokines. These, in turn, stimulate mesangial cells, fibroblasts, and tubular epithelial cells to undergo phenotypic activation or transition and produce a large amount of extra cellular matrix (ECM) components. A TG2 inhibitor of the invention, alone or in combination with thioredoxin, can be administered to reduce inflammatory damage associated with renal fibrosis.

The compounds of the invention may also find use in the treatment of enteric inflammatory conditions, for example celiac disease, Crohn's disease, inflammatory bowel syndrome, and the like.

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Centigrade, and pressure is at or near atmospheric.

Example 1

Design of Novel Inhibitors

Profiling a library of DHI-based compounds for their inhibition potency towards TG2 and their specificity versus TG1, we found that structures bearing an aromatic amino acid (or a derivative thereof) in the central core, specifically 5-fluorotryptophan were particularly potent against TG2 (as published in (Watts et al., 2006) J. Med. Chem. 49, 7493-7501) but dramatically more so against TG1 (see (Schaertl et al., 2010) J. Biomol. Screen. 15, 478-487), making them unattractive lead compounds. In contrast, compounds bearing cyclic amino acids, specifically proline (e.g. ERW1041E) were only moderately potent against TG2 (as published in (Watts et al., 2006) supra.) but were only comparably potent against TG1 (see (Diraimondo et al., 2013) ACS Chem. Biol.)

Beyond inhibition of TG2, there has been some interest in modulating its activity through its inherent regulatory mechanisms. Ordinarily, extracellular TG2 is in an oxidized state and as such catalytically silent (Siegel et al., 2008 PLoS One 3, e1861; Stamnaes et al., 2010 J. Biol. Chem. 285, 25402-25409), pending its reduction by e.g. the redox protein thioredoxin (TRX) (Jin et al., 2011 J. Biol. Chem. 286, 37866-37873). As such, thioredoxin might be expected to have a pathogenic role in inflammatory conditions where TG2 activity is implicated. Paradoxically, however, TRX might actually be protective in some of these conditions, potentially due to its other anti-inflammatory properties (Tian et al., 2013 Front. Immunol. 4, 269). In fact, a protective role for TRX has been implicated in e.g. sepsis (Hofer et al., 2009 Crit. Care Med. 37, 2155-2159), and ischemic reperfusion injuries (Fukuse et al., 1995 Thorax 50, 387-391; Tao et al., 2004 Proc. Natl. Acad. Sci. U.S.A. 101, 11471-11476), despite its activation of detrimental TG2 activity. Taken together, these studies indicate that thioredoxin in combination with a TG2 inhibitor might be a particularly well suited therapeutic approach towards these diseases.

We therefore hypothesized that we might gain specificity by exploiting the conformational preorganization that cyclic amino acids bestow on the inhibitor, possibly by combining the cyclic nature with aromatic sidechains to gain potency. We made an extensive array of modifications to the proline core, some of which are disclosed in the literature (Diraimondo et al., 2013, supra) but these only furnished marginal improvements in potency and/or specificity.

However, when we attached aromatic moieties at the 4-trans-position of L-proline either directly (in the 4-aryl series) or through an amide linker (in the 4-arylamido-series), we saw a surprising and sharp rise in potency against TG2 without compromising selectivity. In comparison to the previously disclosed inhibitors, it appeared crucial that the aromatic/hydrophobic moiety is attached at the 4-position of the proline core rigidly and without much conformational flexibility. We thus wish to claim TG2 inhibitors with the general structure of FIG. 1, of which the 4-aryl and 4-arylamido series are specific examples:

On the 4-arylamido series (Table 1), we investigated the hydroxyl-substituted series (2-4) and found a similar trend as in the 4-aryl series, where para-hydroxy substitution was optimal, furnishing a potent TG2 inhibitor with modest specificity versus TG1. Moving from the parent phenyl ring (1) to heteroaromatics, we saw a dramatic increase in potency and specificity in the nicotinamido-derivative (5, aka CK996). Adding a second nitrogen in the ring with the pyrazyl-derivative (6) yielded a precipitous drop in potency. Given that the change from pyridine to pyrazine or phenyl is accompanied by a significant decrease or absence of hydrogen bond accepting capacity, we may speculate whether 3-pyridyl allows a new hydrogen bond to be established.

On the 4-aryl series, we wanted to verify that the 4-trans configuration was preferred and indeed, the 4-cis derivative (9) as well as a planar olefin derivative (16) had diminished overall potency. We next introduced hydroxy (10-12) and chloro substituents (13/14) off the aromatic ring and found that the phenols were generally preferable over the chloro derivatives in both their potency and selectivity parameters and that the para-hydroxy-substitution (12) was particularly favorable. Given that earlier studies had shown that tryptophan was the ideal aromatic amino acid and the 5-fluoro substituted derivative a particularly potent inhibitor (Watts et al., 2006), we introduced a 3-(5-fluoro)-indolyl moiety (15), but unfortunately, this modification poorly translated from the open chain amino acid to the proline-derived series.

TABLE 1

| # | R = | $k_{inh}/K_i$ [mM$^{-1}$min$^{-1}$] TG1 | TG2 |
|---|---|---|---|
| 1 | H | 24.6 | 25.8 |
| 2 | o-OH | 27.1 | 37.1 |
| 3 | m-OH | 18.1 | 36.2 |
| 4 | p-OH | 31.3 | 56.4 |
| 5/ CK9966 | 3-pyridyl | 20.0 | 108 |
| 6 | 2-pyrazyl | 12.0 | 15.7 |
| 7 |  | 5.8 | 13.8 |

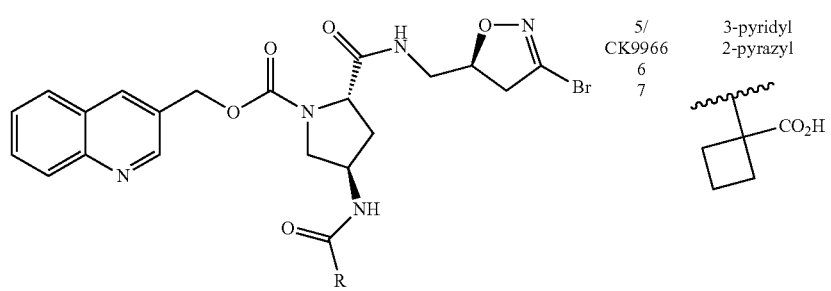

TABLE 1-continued

| # | R = | $k_{inh}/K_i$ [mM$^{-1}$min$^{-1}$] TG1 | TG2 |
|---|-----|------|------|
| 8 | H | 66.3 | 48.6 |
| 9 | H (cis) | 17.2 | 17.7 |
| 10 | o-OH | 29.5 | 33.8 |
| 11 | m-OH | 38.7 | 52.2 |
| 12 | p-OH | 90.7 | 91.1 |
| 13 | m-Cl | 41.7 | 25.3 |
| 14 | p-Cl | 15.4 | 12.0 |
| 15 |  | 48.0 | 18.4 |
| 16 |  | 18.9 | 11.1 |

In vitro potency of TG2 inhibitors against TG2 or TG1: Inhibitors were assayed in the glutamate dehydrogenase-coupled deamidation assay described in the literature (Choi et al., 2005; Day and Keillor, 1999) and inhibitor potencies computed from full progress curves using an irreversible inhibition model as described (Gray and Duggleby, 1989; Hausch et al., 2003). The substrate for TG2 was the protected dipeptide Cbz-Gln-Gly as described and for TG1, its derivative Cbz-Gln-Ser.

TG2 is Rapidly Activated in the LPS-Induced Murine Endotoxemia Model and can be Inhibited with Intraperitoneal CK996.

Figure 2:
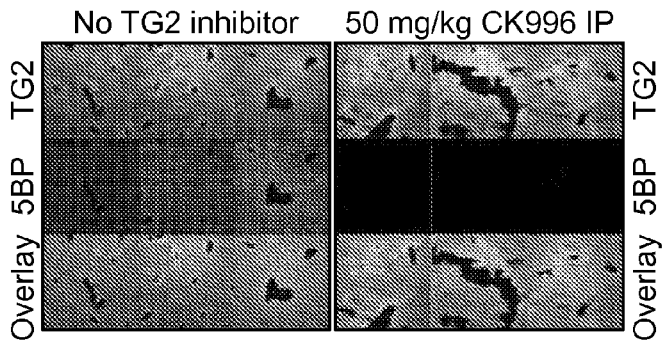
FIG. 2: TG2 is active in septic mice and can be inhibited by the intraperitoneal administration of 50 mg/kg CK996: Panels (A) through (C) depict tissues from the liver, lung and small intestine from septic male BL6 mice that were stained for TG2 protein (top row) or TG2 activity (middle row). The bottom row depicts the merged images from the TG2 protein and activity channel, respectively. Tissues from mice that had received the TG2 inhibitor CK996 are shown in the right set of images in each panel whereas tissues from control mice that received vehicle only are shown in the left set of images. Panel (D) quantifies the ratio of TG2 activity to TG2 protein signal intensity. All mice in this study received lipopolysaccharide (LPS, 5 mg/kg i.v., at t=0) and the TG2 activity-based probe 5-biotinamidopentylamine (5-BP, 100 mg/kg i.p., at t=0 and 90 min)(Dafik et al., 2012; Siegel et al., 2008). One cohort of mice additionally received an intraperitoneal dose of the TG2 inhibitor CK996 (50 mg/kg i.p., at t=0 and 60 min) in vehicle (PBS with 10% DMSO and 2% 2,6-di-(OMe)-beta-cyclodextrin), whereas the control mice received the vehicle alone. At 3 hours the mice were euthanized, tissues collected and frozen in OCT medium and then TG2 protein and activity (5-BP) stained, imaged and quantified as described in the literature (Diraimondo et al., 2013 ACS Chem. Biol.).
Figure 2:
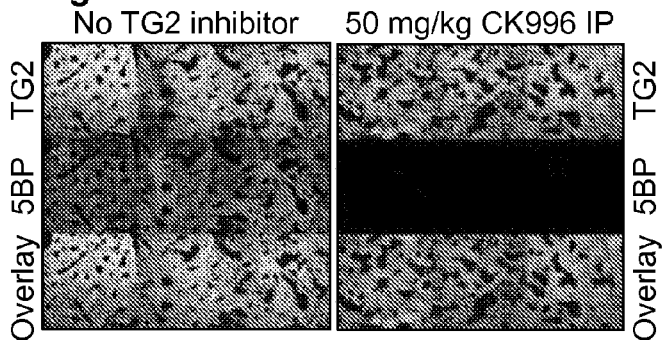
Figure 2:
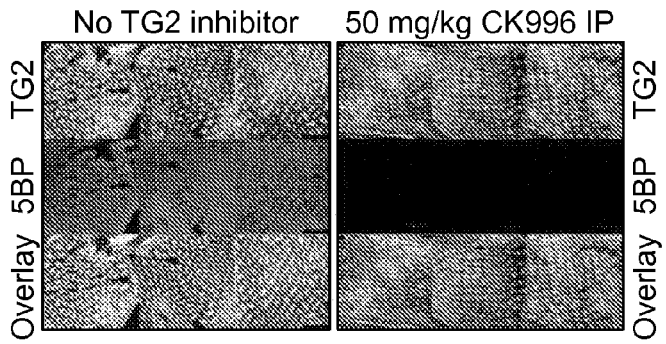
Figure 2:
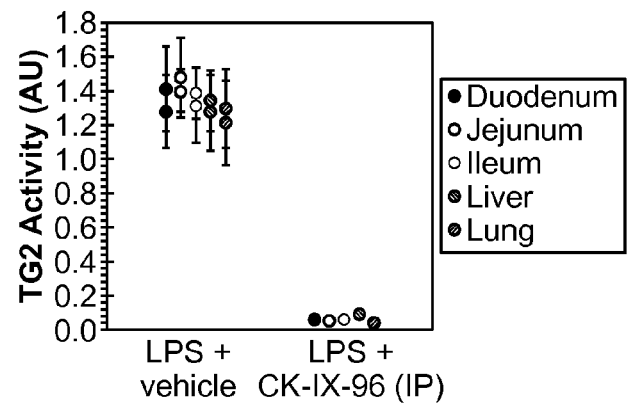

Studies on TG2$^{-/-}$ mice suggested a role for TG2 in the pathogenesis of endotoxic shock (Falasca et al., 2008 J. Immunol. 180, 2616-2624) and we sought to determine whether TG2 activity is induced in the process. Using 5-biotinamidopentylamine (5-BP) as an established probe for TG2 activity in vivo (Dafik et al., 2012 PLoS One 7, e30642; Siegel et al., 2008 PLoS One 3, e1861), we discovered that intraveneous injection of lipopolysaccharide (LPS, 5 mg/kg) to mice induces rapid activation of transglutaminase 2 in their intestines, livers and lungs (FIG. 2). Administering CK996 intraperitoneally (50 mg/kg) to septic mice fully suppressed TG2 activity in these organs demonstrating the utility of this compound for the inhibition of TG2 in vivo.

Administration of CK996 Reduces Proinflammatory Cytokine Load in the LPS-Induced Model of Murine Sepsis.

Figure 3:
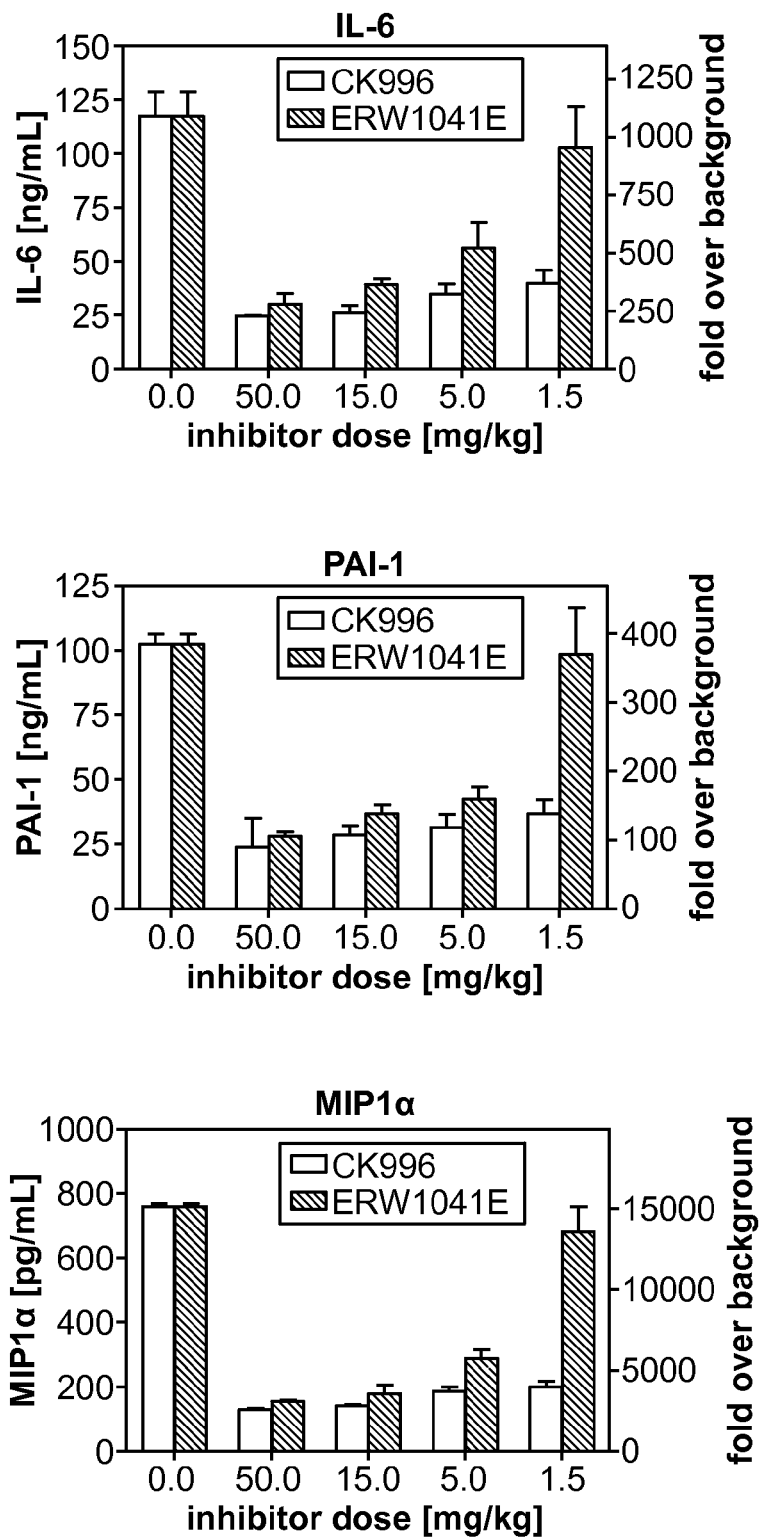
FIG. 3: The TG2 inhibitor CK996 reduces the proinflammatory cytokine load in septic mice at doses as low as 1.5 mg/kg: The graphs display the absolute circulating levels of the proinflammatory cytokines IL-6, PAI-1 and MIP1α in septic male BL6 mice as a function of the dose of intraperitoneally administered CK996 or ERW1041E. In each graph, the right y-axis depicts the relative levels of the respective cytokines over their background level in our control cohort. All septic mice in this study received lipopolysaccharide (LPS, 5 mg/kg i.v., at t=0) and either a TG2 inhibitor (CK996 or ERW1041E at 50, 15, 5.0 and 1.5 mg/kg i.p., at t=0 and 60 min) in vehicle (PBS with 5% DMSO, 2% Tween-80 and 2.5% hydroxypropyl-beta-cyclodextrin) or, for the septic control cohort, vehicle alone. An additional cohort defining the baseline cytokine levels received only intravenous vehicle and intraperitoneal inhibitor vehicle, respectively. At 3 hours the mice were euthanized and plasma collected in lithium heparin tubes. The levels of the respective proinflammatory cytokines were quantified using commercial ELISA kits according to the manufacturers' instructions.

Having established that intraperitoneal administration of CK996 could suppress TG2 activity in septic mice, we next sought to determine whether this pharmacologic intervention had any effect on the circulating levels of the key proinflammatory cytokines in sepsis. To this end, we administered CK996 in doses of 1.5, 5.0, 15 or 50 mg/kg intraperitoneally to septic mice (5 mg/kg LPS, iv) and measured the level of the proinflammatory cytokines IL-6, PAI-1 and MIP1α in plasma that was collected at 3 hours after infusion of LPS. CK996 dramatically reduced the circulating levels of these three cytokines at all doses tested, whereas ERW1041E, when administered at the same doses had no effect at the 1.5 mg/kg level (FIG. 3).

This experiment demonstrated the superior potency of CK996 compared to ERW1041E in vivo, its efficacy in reducing proinflammatory cytokines in endotoxemia and the therapeutic benefit of TG2 inhibition in this condition as judged by the proinflammatory cytokine biomarkers.

Combination Therapy of CK996 and Human Thioredoxin Reduces Proinflammatory Cytokine Load in the LPS-Induced Model of Murine Sepsis.

Given that inhibition of TG2 reduced the proinflammatory cytokine load in endotoxemia, we investigated the role of thioredoxin (TRX). Extracellular TG2 is typically catalytically silent (Siegel et al., 2008, supra) and we have shown that reduced thioredoxin activates oxidized TG2 (Jin et al., 2011 J. Biol. Chem. 286, 37866-37873), which would argue for a detrimental role for TRX. In contrast, data from patients and mouse models of sepsis argues for a protective role (Hofer et al., 2009 Crit. Care Med. 37, 2155-2159).

Figure 4:
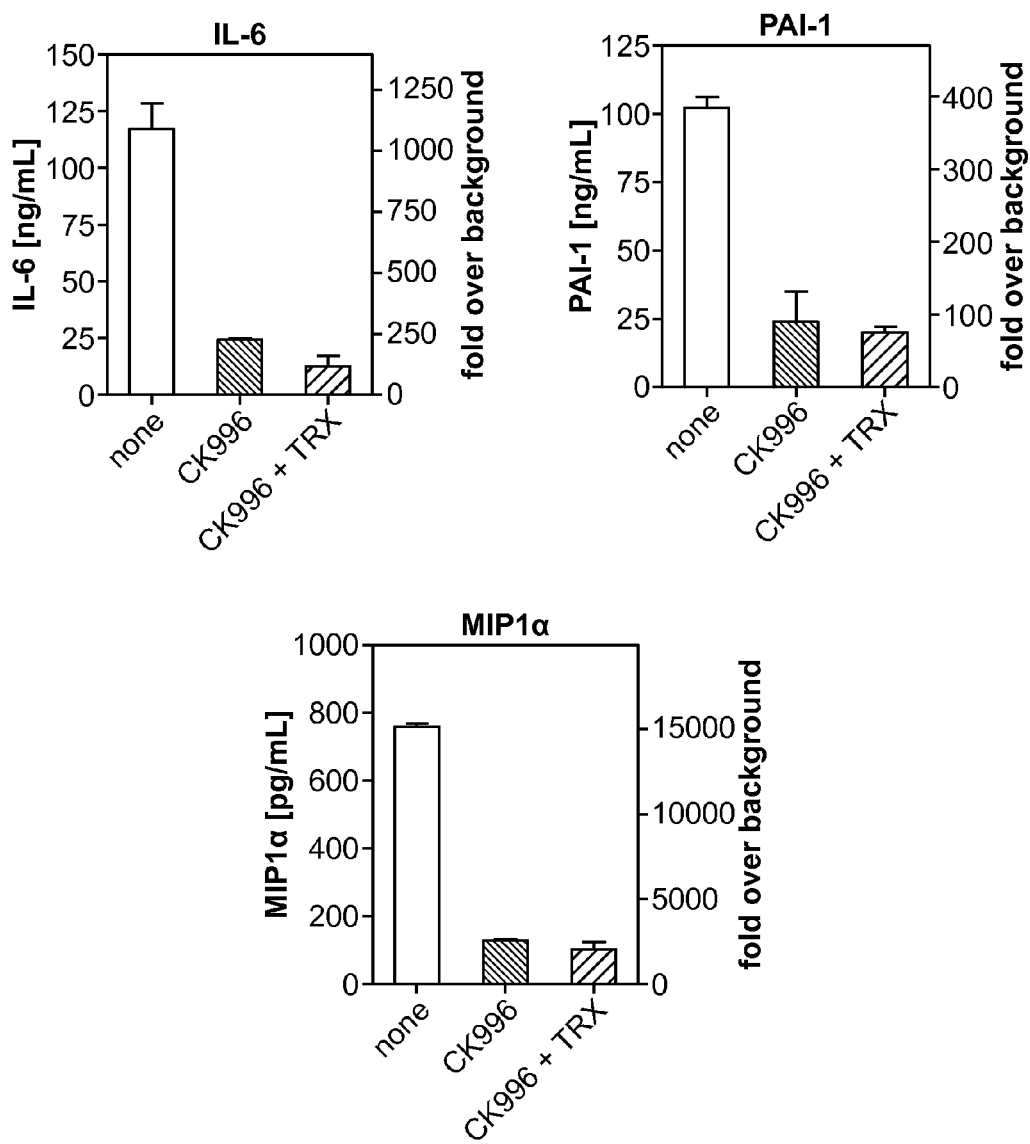
FIG. 4: The TG2 inhibitor CK996 and recombinant human thioredoxin protein cooperatively reduce the proinflammatory cytokine load in septic mice: The graphs display the absolute circulating levels of the proinflammatory cytokines IL-6, PAI-1 and MIP1α in septic male BL6 mice that had received either CK996 (50 mg/kg) alone, a combination of CK996 (50 mg/kg) and recombinant human thioredoxin protein (10 mg/kg) or vehicle only. The experiment was conducted as described in FIG. 3. The mice in the combination therapy cohort received a dose of recombinant human thioredoxin (TRX, 10 mg/kg i.p., at 0 and 60 min) in addition to CK996 as described above. TRX was expressed, purified and prepared as described in the literature (Jin et al., 2011 J. Biol. Chem. 286, 37866-37873).

We therefore co-administered recombinant human thioredoxin protein (10 mg/kg, ip) along with CK996 (50 mg/kg, ip) to septic mice (5 mg/kg, iv) and quantified the load of proinflammatory cytokines as above. Surprisingly, we found a cooperative effect of the two interventions, where the combination therapy of TRX and CK996 suppressed the proinflammatory cytokines more than CK996 alone (FIG. 4), arguing for the therapeutic benefit of this combination in sepsis.

General Procedure for the Preparation of TG2 inhibitors. The inhibitors were prepared analogously to the method reported in the literature (Diraimondo et al., 2013, supra):

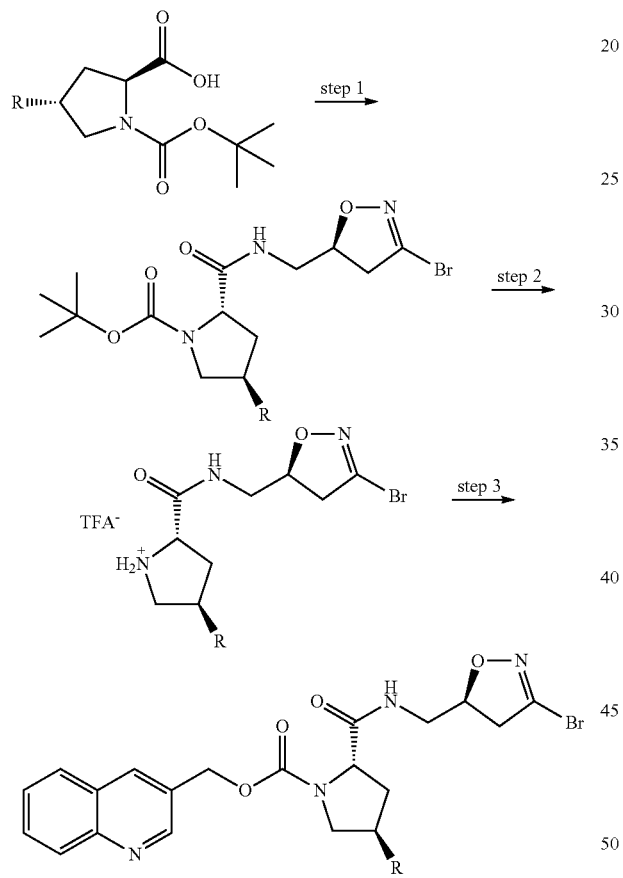

Step 1:
The BOC-protected amino acid (1 eq.), EDCI HCl (1.15 eq.), HOBt hydrate (1 eq.) and (S)-(3-bromo-4,5-dihydroisoxazol-5-yl)methanamine (1 eq.), prepared by our modification (Diraimondo et al., 2013) of the procedure of Rohloff and coworkers (Rohloff et al., 1992 Tetrahedron Lett. 33, 3113-3116) are dissolved in DMF (to approximately 150 mM) and N-Methylmorpholine (2 eq.) is added. The mixture is stirred for 30 minutes and then diluted with approximately 10 volumes of water and extracted with 10 volumes of ethyl acetate. The organic layer is washed with 10 volumes of sodium bicarbonate twice, followed by 10 volumes of brine, dried over sodium sulfate and evaporated. The product is typically obtained as a viscous oil.

Step 2:
The crude product is taken up in trifluoroacetic acid (to approximately 170 mM) and stirred for 30 minutes, before the acid is carefully evaporated. The resulting viscous oil is taken up in an equal volume (relative to TFA) of DCM and the volatiles evaporated again. This procedure is repeated with anhydrous methanol. Drying the sample under vacuum furnishes the intermediate as an oil or foam, which is used directly in the next step.

Step 3:
The intermediate is then dissolved in anhydrous DMF to approximately 150 mM and triethylamine (1 eq.) and DMAP (0.1 eq.) are added. Separately, quinolin-3-ylmethyl 1H-imidazole-1-carboxylate (1 eq.), which is prepared as previously described (Diraimondo et al., 2013), is dissolved in anhydrous DCM to approximately 300 mM and the two solutions are then combined. The mixture is stirred at room temperature overnight, and then the volatiles are removed under reduced pressure. The residue is diluted with approximately 10 volumes of water (relative to DMF) and extracted with 10 volumes of ethyl acetate. Again, the organic layer is washed with 10 volumes of sodium bicarbonate twice, followed by 10 volumes of brine, dried over sodium sulfate and evaporated. The crude product is typically purified by silica gel chromatography with a gradient of 80-100% ethyl acetate in pentane, followed by 0-10% methanol in ethyl acetate or by preparative reverse-phase HPLC in a gradient of acetonitrile in water with 0.1% TFA as acidic modifier.

(2S,4R)-quinolin-3-ylmethyl 4-benzamido-2-((((S)-3-bromo-4,5-dihydroisoxazol-5-yl)methyl)carbamoyl)pyrrolidine-1-carboxylate (1)

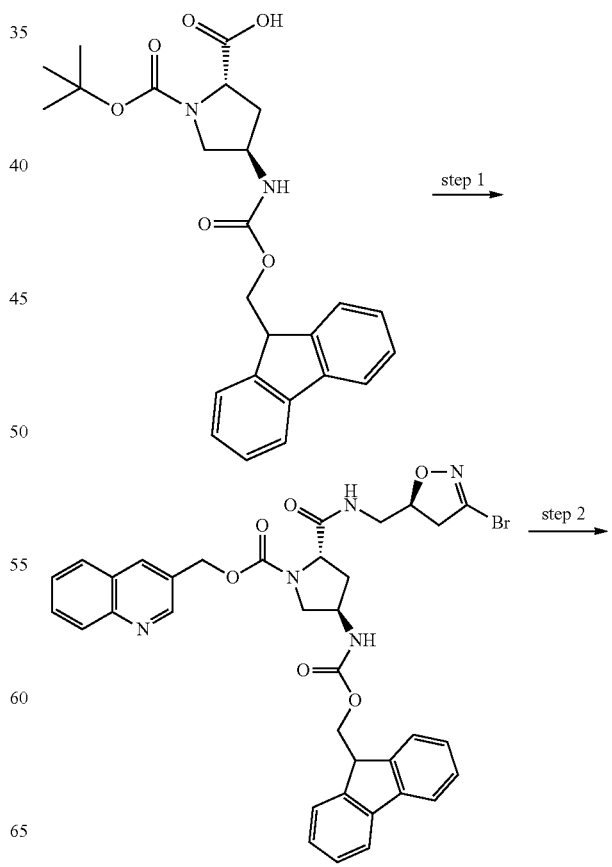

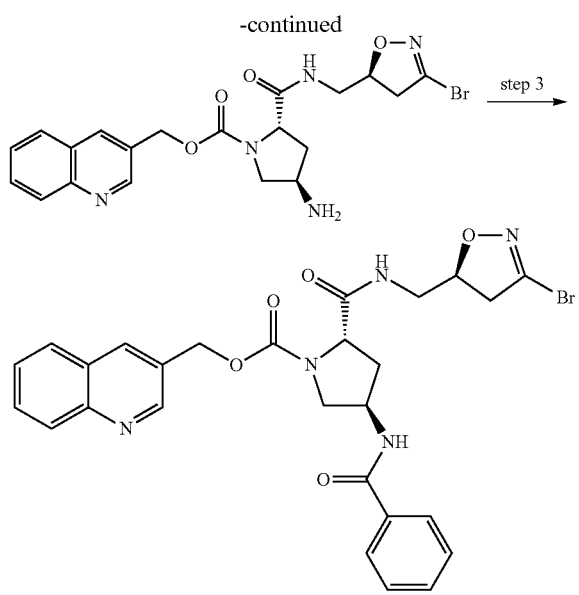

Step 1—(2S,4R)-quinolin-3-ylmethyl 4-((((9H-fluoren-9-yl)methoxy)carbonyl)amino)-2-((((S)-3-bromo-4,5-dihydroisoxazol-5-yl)methyl)carbamoyl)pyrrolidine-1-carboxylate: Adapting the general procedure, (2S,4R)-4-((((9H-fluoren-9-yl)methoxy)carbonyl)amino)-1-(tert-butoxycarbonyl)pyrrolidine-2-carboxylic acid (1.2 g, 2.65 mmol), EDCI (0.585 g, 3.05 mmol) and HOBt (0.358 g, 2.65 mmol) were dissolved in 5 mL DMF, stirred for 10 minutes and (S)-(3-bromo-4,5-dihydroisoxazol-5-yl)methanamine (0.475 g, 2.65 mmol) was added. The mixture was allowed to react for 4 hours before 25 mL of water were added whereby a greasy precipitate formed. The mixture was allowed to sit for 1 hour before the liquid portion was decanted off and the greasy solid material dissolved in 40 mL of ethyl acetate. The ethyl acetate was washed with brine and the dried over sodium sulfate before it was evaporated, affording (2S,4R)-tert-butyl 4-((((9H-fluoren-9-yl)methoxy)carbonyl)amino)-2-((((S)-3-bromo-4,5-dihydroisoxazol-5-yl)methyl)carbamoyl)pyrrolidine-1-carboxylate (1.3 g, 2.119 mmol, 80 yield) which was elaborated to the title compound using steps 2 and 3 of the general procedure.

Step 2—(2S,4R)-quinolin-3-ylmethyl 4-amino-2-((((S)-3-bromo-4,5-dihydroisoxazol-5-yl)methyl)carbamoyl)pyrrolidine-1-carboxylate: The intermediate from the previous step was deprotected using piperidine in DCM (1:1) and stirring the mixture for 30 minutes. All volatiles were then removed under reduced pressure and the residue purified by silica gel chromatography. The product co-eluted with a decomposition product where bromide had been displaced by piperidine. Given that these were more easily separated after the next reaction, the product was taken forward as an impure mixture, but could be purified by preparative reverse-phase HPLC, if desired.

Step 3—(2S,4R)-quinolin-3-ylmethyl 4-benzamido-2-((((S)-3-bromo-4,5-dihydroisoxazol-5-yl)methyl)carbamoyl)pyrrolidine-1-carboxylate: The intermediate from the previous step was coupled to benzoic acid using a similar procedure as step 1 in the synthesis of compound (5). The final product was purified by preparative TLC. $^1$H NMR (500 MHz, DMSO-d$_6$, mixture of rotational isomers) δ 8.93 & 8.86 (2 d, J=2.2 Hz, 1H), 8.65 (t, J=7.3 Hz, 1H), 8.57 & 8.51 (2 t, J=6.0 Hz, 1H), 8.36 & 8.28 (2 d, J=1.1 Hz, 1H), 8.03 (d, J=8.4 Hz, 1H), 8.01-7.93 (m, 1H), 7.84-7.80 (m, 2H), 7.77 (ddd, J=8.4, 6.9, 1.5 Hz, 1H), 7.67-7.60 (m, 1H), 7.56-7.50 (m, 1H), 7.50-7.44 (m, 2H), 5.35-5.20 (m, 2H), 4.75-4.67 & 4.57-4.48 (2 m, 2H), 4.38 & 4.29 (2 dd, J=8.6, 5.7 Hz, 1H), 3.84 & 3.78 (2 dd, J=10.6, 6.5 Hz, 1H), 3.50-3.10 (m, 4H), 3.00 & 2.91 (2 dd, J=17.5, 7.5 Hz, 1H), 2.62-2.45 (m, 1H, partly obscured by solvent), 1.96-1.85 (m, 1H). HRMS (ESI-QTOF) m/z: calculated for C$_{27}$H$_{27}$BrN$_5$O$_5^+$ [M+H]$^+$ 580.11901. found 580.11789.

(2S,4R)-quinolin-3-ylmethyl 2-((((S)-3-bromo-4,5-dihydroisoxazol-5-yl)methyl) carbamoyl)-4-(2-hydroxybenzamido)pyrrolidine-1-carboxylate (2). The title compound was prepared analogously to compound (1) but with only one equivalent of all reagents relative to the amine and purified by preparative TLC. $^1$H NMR (500 MHz, DMSO-d$_6$, mixture of rotational isomers) δ 12.33 (d, J=3.0 Hz, 1H), 8.96 (t, J=7.0 Hz, 1H), 8.94 & 8.86 (2 d, J=2.2 Hz, 1H), 8.58 & 8.52 (2 t, J=6.0 Hz, 1H), 8.36 & 8.28 (2 d, 1.5 & 2.2 Hz, 1H), 8.06-7.94 (m, 2H), 7.82-7.73 (m, 2H), 7.63 (tdd, J=6.9, 4.5, 1.3 Hz, 1H), 7.40 (td, J=7.7, 1.7 Hz, 1H), 6.93-6.86 (m, 2H), 5.37-5.20 (m, 2H), 4.75-4.67 & 4.62-4.49 (2 br m, 2H), 4.39 & 4.30 (2 dd, J=8.8, 5.3 Hz, 1H), 3.86 & 3.80 (dd, J=10.7, 6.5 Hz, 1H), 3.46 (ddd, J=31.0, 10.6, 5.1 Hz, 1H), 3.39-3.09 (m, 3H), 2.99 & 2.91 (2 dd, J=17.5, 7.4 Hz, 1H), 2.66-2.51 (m, 1H), 1.97-1.85 (m, 1H).

(2S,4R)-quinolin-3-ylmethyl 2-((((S)-3-bromo-4,5-dihydroisoxazol-5-yl)methyl) carbamoyl)-4-(3-hydroxybenzamido)pyrrolidine-1-carboxylate (3). The title compound was prepared analogously to compound (1), but with only one equivalent of all reagents relative to the amine and purified by preparative TLC. $^1$H NMR (500 MHz, DMSO-d$_6$, mixture of rotational isomers) δ 10.31 (br s, 1H), 8.93 & 8.85 (2 d, J=2.2 Hz, 1H), 8.67-8.50 (m, 2H), 8.36 & 8.28 (2 d, J=1.5 & 2.2 Hz, 1H), 8.12-7.89 (m, 2H), 7.77 (ddd, J=8.4, 6.9, 1.5 Hz, 1H), 7.67-7.60 (m, 1H), 7.31-7.14 (m, 3H), 6.92 (dt, J=7.2, 2.4 Hz, 1H), 5.36-5.20 (m, 2H), 4.82-4.41 (m, 2H), 4.32 (ddd, J=48.9, 8.6, 5.6 Hz, 1H), 3.79 (ddd, J=31.9, 10.6, 6.5 Hz, 1H), 3.53-3.19 (m, 3H), 3.18-3.09 (m, 1H), 2.96 (ddd, J=43.1, 17.5, 7.3 Hz, 1H), 2.58-2.44 (m, 1H, partly obscured by solvent), 2.03-1.83 (m, 1H). HRMS (ESI-QTOF) m/z: calculated for C$_{27}$H$_{27}$BrN$_5$O$_6^+$ [M+H]$^+$ 596.11392. found 596.11284.

(2S,4R)-quinolin-3-ylmethyl 2-((((S)-3-bromo-4,5-dihydroisoxazol-5-yl)methyl) carbamoyl)-4-(4-hydroxybenzamido)pyrrolidine-1-carboxylate (4). The title compound was prepared analogously to compound (5). It is noteworthy that the title compound precipitated from an ethyl acetate solution of the crude final material in high purity and satisfactory yield (200 mg, 0.335 mmol, 18.8% yield over 5 steps), obviating the need for a chromatographic purification step. $^1$H NMR (500 MHz, DMSO-d$_6$, mixture of rotational isomers) δ 10.10 (br s, 1H), 8.93 & 8.85 (2 d, J=2.2 Hz, 1H), 8.56 & 8.49 (2 t, J=6.0 Hz, 1H), 8.38 (t, J=7.3 Hz, 1H), 8.35 & 8.28 (2 d, J=1.3 Hz, 1H), 8.03 (d, J=8.4 Hz, 1H), 7.98 (ddd, J=10.1, 8.3, 1.4 Hz, 1H), 7.77 (ddd, J=8.4, 6.9, 1.5 Hz, 1H), 7.68 (dd, J=8.6, 5.4 Hz, 2H), 7.66-7.60 (m, 1H), 6.79 (dd, J=8.7, 2.9 Hz, 2H), 5.39-5.18 (m, 2H), 4.76-4.66 & 4.56-4.44 (2 m, 2H), 4.36 & 4.27 (2 dd, J=8.6, 5.8 Hz, 1H), 3.82 & 3.75 (2 dd, J=10.5, 6.4 Hz, 1H), 3.52-3.27 (m, 2H, partly obscured by residual water), 3.26-3.10 (m, 2H), 2.99 & 2.91 (2 dd, J=17.5, 7.5 Hz, 1H), 2.57-2.43 (m, 1H, partly obscured by solvent), 1.92-1.80 (m, 1H). HRMS (ESI-QTOF) m/z: calculated for C$_{27}$H$_{27}$BrN$_5$O$_6^+$ [M+H]$^+$ 596.11392. found 596.11375.

(2S,4R)-quinolin-3-ylmethyl 2-((((S)-3-bromo-4,5-dihydroisoxazol-5-yl)methyl)carbamoyl)-4-(nicotinamido)pyrrolidine-1-carboxylate (5)

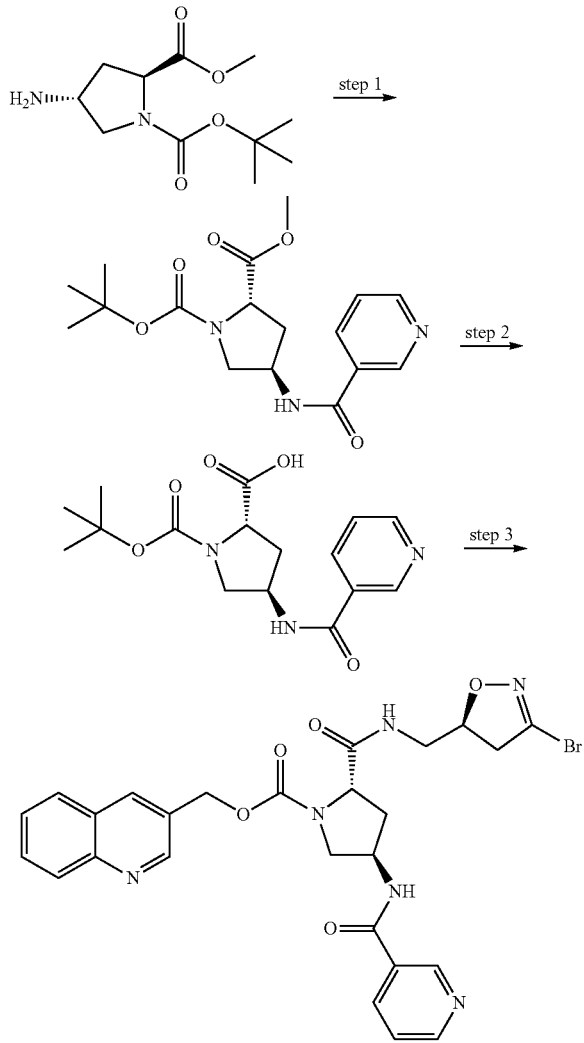

Step 1—(2S,4R)-1-tert-butyl 2-methyl 4-(nicotinamido)pyrrolidine-1,2-dicarboxylate: Commercial (2S,4R)-1-tert-butyl 2-methyl 4-aminopyrrolidine-1,2-dicarboxylate, HCl (500 mg, 1.781 mmol), nicotinic acid (439 mg, 3.56 mmol), EDC HCl (683 mg, 3.56 mmol) and HOBt (241 mg, 1.781 mmol) were dissolved in 10 mL DMF and N-Methylmorpholine (392 µl, 3.56 mmol) was added. The mixture was stirred at room temperature overnight before it was diluted with 100 mL water and extracted with 100 mL ethyl acetate. The organic layer was washed with 100 mL aqueous sodium bicarbonate solution twice, followed by 100 mL brine. After drying the organic layer over sodium sulfate, the volatiles were removed under reduced pressure, furnishing the product as yellowish oil.

Step 2—(2S,4R)-1-(tert-butoxycarbonyl)-4-(nicotinamido)pyrrolidine-2-carboxylic acid: To saponify the methyl ester, the intermediate was dissolved in THF (30 mL) and methanol (10 mL) and aqueous lithium hydroxide (1 M) was added in portions while the reaction progress was monitored by TLC. Upon completion, an equimolar amount of aqueous hydrochloric acid (1 M) was added and the volatiles evaporated. The mixture was diluted with water to about 50 mL and the pH adjusted to 4-5. The mixture was then extracted with ethyl acetate (6*50 mL). The combined organic fractions were dried over sodium sulfate and evaporated under reduced pressure, furnishing (2S,4R)-1-(tert-butoxycarbonyl)-4-(nicotinamido)pyrrolidine-2-carboxylic acid (498 mg, 1.485 mmol, 83 yield over steps 1 & 2).

Step 3—(2S,4R)-quinolin-3-ylmethyl 2-((((S)-3-bromo-4,5-dihydroisoxazol-5-yl)methyl)carbamoyl)-4-(nicotinamido)pyrrolidine-1-carboxylate: The BOC-protected amino acid thus obtained was used without further purification and elaborated to the final inhibitor using the general procedure and purified by silica gel chromatography (80% to 100% ethyl acetate in pentane followed by 0-10% methanol in ethyl acetate), furnishing (2S,4R)-quinolin-3-ylmethyl 2-((((S)-3-bromo-4,5-dihydroisoxazol-5-yl)methyl)carbamoyl)-4-(nicotinamido)pyrrolidine-1-carboxylate (171 mg, 0.294 mmol, 19.8% yield over 3 steps). $^1$H NMR (500 MHz, DMSO-$d_6$, mixture of rotational isomers) δ 8.97 (ddd, J=6.7, 2.3, 0.9 Hz, 1H), 8.94 & 8.86 (2 d, J=2.2 Hz, 1H), 8.83 (t, J=6.8 Hz, 1H), 8.72-8.69 (m, 1H), 8.56 & 8.50 (2 t, J=6.0 Hz, 1H), 8.36 & 8.28 (2 d, J=1.3 Hz, 1H), 8.18-8.13 (m, 1H), 8.03 (d, J=8.4 Hz, 1H), 7.99 (dd, J=13.6, 8.2 Hz, 1H), 7.77 (ddd, J=8.4, 6.9, 1.4 Hz, 1H), 77.67-7.60 (m, 1H), 7.54-7.48 (m, 1H), 5.39-5.18 (m, 2H), 4.77-4.65 & 4.58-4.48 (2 m, 2H), 4.38 & 4.29 (2 dd, J=8.5, 6.0 Hz, 1H), 3.86 & 3.80 (2 dd, J=10.6, 6.6 Hz, 1H), 3.50-3.28 (m, 2H, partly obscured by residual water), 3.27-3.11 (m, 2H), 2.99 & 2.91 (2 dd, J=17.5, 7.5 Hz, 1H), 2.60-2.50 (m, 1H, partly obscured by solvent), 1.98-1.87 (m, 1H). HRMS (ESI-QTOF) m/z: calculated for $C_{26}H_{27}BrN_6O_5^{2+}$ [M+2H]$^{2+}$ 291.06077. found 291.06076.

(2S,4R)-quinolin-3-ylmethyl 2-((((S)-3-bromo-4,5-dihydroisoxazol-5-yl)methyl)carbamoyl)-4-(pyrazine-2-carboxamido)pyrrolidine-1-carboxylate (6). The title compound was prepared analogously to compound (1) and purified by preparative TLC. $^1$H NMR (500 MHz, DMSO-$d_6$, mixture of rotational isomers) δ 9.23 (dd, J=8.8, 5.0 Hz, 1H), 9.18 (dd, J=4.6, 1.5 Hz, 1H), 8.94 & 8.86 (2 d, J=2.2 Hz, 1H), 8.87 (d, J=2.5 Hz, 1H), 8.73 (dd, J=2.5, 1.5 Hz, 1H), 8.61 & 8.56 (2 t, J=6.0 Hz, 1H), 8.37 & 8.28 (2 d, J=2.1 Hz, 1H), 8.03 (dd, J=8.5, 2.7 Hz, 1H), 7.99 (ddd, J=12.7, 8.3, 1.4 Hz, 1H), 7.78 (ddd, J=8.4, 6.8, 1.5 Hz, 1H), 7.67-7.60 (m, 1H), 5.37-5.19 (m, 2H), 4.76-4.64 & 4.60-4.52 (2 br m, 2H), 4.42 & 4.34 (2 dd, J=9.0, 4.0 Hz, 1H), 3.85 & 3.78 (2 dd, J=10.9, 6.3 Hz, 1H), 3.59-3.38 (m, 2H), 3.31-3.08 (m, 2H), 3.04-2.85 (m, 1H), 2.67-2.53 (m, 1H), 1.93-1.82 (m, 1H).

1-(((3R,5S)-5-((((S)-3-bromo-4,5-dihydroisoxazol-5-yl)methyl)carbamoyl)-1-((quinolin-3-ylmethoxy)carbonyl)pyrrolidin-3-yl)carbamoyl)cyclobutanecarboxylic acid, TFA salt (7). The title compound was prepared analogously to compound (1) but with a fivefold excess of all reagents relative to the amine. The solvent was evaporated from the crude amide coupling mixture under vacuum and the residue directly purified by reverse-phase HPLC, furnishing the title compound as its TFA salt. $^1$H NMR (500 MHz, DMSO-$d_6$, mixture of rotational isomers) δ 9.02-8.87 (m, 1H), 8.58-8.33 (m, 2H), 8.09-7.92 (m, 3H), 7.87-7.79 (m, 1H), 7.69 (ddd, J=8.1, 7.0, 1.2 Hz, 1H), 5.41-5.19 (m, 2H), 4.80-4.66 & 4.61-4.50 (2 br m, 1H), 4.44-4.17 (m, 2H), 3.73 (ddd, J=34.3, 10.6, 6.5 Hz, 1H), 3.53-3.09 (m, 4H), 2.96 (ddd, J=39.5, 17.5, 7.5 Hz, 1H), 2.81-2.70 (m, 1H), 2.47-2.25 (m, 4H), 1.93-1.66 (m, 3H).

(2S,4S)-quinolin-3-ylmethyl 2-((((S)-3-bromo-4,5-dihydroisoxazol-5-yl)methyl)carbamoyl)-4-phenylpyrrolidine-1-carboxylate (8). Commercial (2S,4S)-1-(tert-butoxycarbonyl)-4-phenylpyrrolidine-2-carboxylic acid was elaborated into the final inhibitor using the general procedure, furnishing (2S,4S)-quinolin-3-ylmethyl 2-((((S)-3-bromo-4,5-dihydroisoxazol-5-yl)methyl)carbamoyl)-4-phenylpyrrolidine-1-carboxylate (81 mg, 0.151 mmol, 43.9% yield over three steps) as a white solid. $^1$H NMR (400 MHz, DMSO-d$_6$, mixture of rotational isomers) δ 8.93 & 8.85 (2 d, J=2.2 Hz, 1H), 8.46-8.24 (m, 2H), 8.07-7.94 (m, 2H), 7.77 (ddd, J=8.4, 6.9, 1.5 Hz, 1H), 7.67-7.60 (m, 1H), 7.35-7.27 (m, 3H), 7.27-7.19 (m, 1H), 5.39-5.21 (m, 2H), 4.81-4.58 (m, 1H), 4.46 & 4.37 (dd, J=8.6, 1.8 Hz, 1H), 4.03-3.87 (m, 1H), 3.55-3.17 (m, 5H), 3.04 (ddd, J=21.1, 17.6, 7.2 Hz, 1H), 2.44-2.29 (m, 1H), 2.13 (td, J=13.5, 6.3 Hz, 1H). HRMS (ESI-QTOF) m/z: calculated for C$_{26}$H$_{26}$BrN$_4$O$_4{}^+$ [M+H]$^+$ 537.11319. found 537.11310.

(2S,4R)-quinolin-3-ylmethyl 2-((((S)-3-bromo-4,5-dihydroisoxazol-5-yl)methyl)carbamoyl)-4-phenylpyrrolidine-1-carbon/late (9). (S)-1-(tert-butoxycarbonyl)-4-phenyl-2,5-dihydro-1H-pyrrole-2-carboxylic acid was prepared analogously to steps 1 and 2 of compound (12). Similar to the procedure by Krapcho and coworkers (Krapcho et al., 1988), an aliquot (64 mg, 0.221 mmol) was dissolved in 10 mL ethanol (200 Proof) and Palladium 10% on carbon (23.5 mg, 0.022 mmol) was added. The round bottom flask was capped with a septum and purged with hydrogen gas briefly and kept under a slight positive pressure of hydrogen while stirring overnight. The reaction mixture was then filtered through a small layer of silica gel sandwiched between layers of sand in a pipette column. The matrix was washed with additional ethanol and the combined filtrate was evaporated under reduced pressure, yielding (2S,4R)-1-(tert-butoxycarbonyl)-4-phenylpyrrolidine-2-carboxylic acid (50 mg, 0.172 mmol, 78% yield) which was then elaborated to the final inhibitor using the general procedure. $^1$H NMR (500 MHz, DMSO-d6) δ 8.97-8.84 (m, 1H), 8.45-8.38 (m, 1H), 8.37 & 8.28 (2 s, 1H), 8.11-7.91 (m, 2H), 7.77 (tt, J=8.2, 1.3 Hz, 1H), 7.67-7.60 (m, 1H), 7.37-7.21 (m, 5H), 5.38-5.19 (m, 2H), 4.79-4.52 (m, 1H), 4.42-4.23 (m, 1H), 4.13-3.97 (m, 1H), 3.53-2.90 (m, 6H), 2.70-2.53 (m, 1H), 1.94-1.79 (m, 1H). HRMS (ESI-QTOF) m/z: calculated for C$_{26}$H$_{26}$BrN$_4$O$_4{}^+$ [M+H]$^+$ 537.11319. found 537.11291.

(2S,4S)-quinolin-3-ylmethyl 2-((((S)-3-bromo-4,5-dihydroisoxazol-5-yl)methyl)carbamoyl)-4-(2-hydroxyphenyl)pyrrolidine-1-carboxylate, TFA salt (10). The title compound was prepared analogously to compound (12) but with one equivalent of HBTU in place of EDC HCl and HOBt as the amide coupling reagent in step 4 and purified by reverse phase HPLC, furnishing the title compound as its TFA salt. $^1$H NMR (400 MHz, DMSO-d$_6$, mixture of rotational isomers) δ 9.52 (br s, 1H), 8.97 & 8.89 (2 d, J=2.1 Hz, 1H), 8.46-8.28 (m, 2H), 8.08-7.97 (m, 2H), 7.81 (ddd, J=8.5, 6.9, 1.4 Hz, 1H), 7.70-7.61 (m, 1H), 7.09 (dd, J=7.7, 1.6 Hz, 1H), 7.06-6.98 (m, 1H), 6.79 (ddd, J=7.2, 5.7, 1.2 Hz, 1H), 6.76-6.65 (m, 1H), 5.38-5.18 (m, 2H), 4.73 & 4.59 (2 m, 1H), 4.42 & 4.32 (2 dd, J=8.7, 3.1 Hz & 8.8, 2.6, 1H), 3.92 & 3.84 (2 dd, J=10.0, 7.6 Hz, 1H), 3.66 (dt, J=15.8, 8.0 Hz, 1H), 3.46-3.29 (m, 2H), 3.30-2.91 (m, 3H), 2.46-2.30 (m, 1H), 2.12-1.97 (m, 1H). HRMS (ESI-QTOF) m/z: calculated for C$_{26}$H$_{26}$BrN$_4$O$_5{}^+$ [M+H]$^+$ 553.10811. found 553.10765.

(2S,4S)-quinolin-3-ylmethyl 2-((((S)-3-bromo-4,5-dihydroisoxazol-5-yl)methyl)carbamoyl)-4-(3-hydroxyphenyl)pyrrolidine-1-carboxylate, TFA salt (11). The title compound was prepared analogously to compound (12) but with one equivalent of HBTU in place of EDC HCl and HOBt as the amide coupling reagent in step 4 and purified by reverse phase HPLC, furnishing the title compound as its TFA salt. $^1$H NMR (400 MHz, DMSO-d$_6$, mixture of rotational isomers) δ 9.37 (br s, 1H), 8.99 & 8.90 (2 s, 1H), 8.48-8.29 (m, 2H), 8.10-7.94 (m, 2H), 7.85-7.76 (m, 1H), 7.66 (d, J=8.9 Hz, 1H), 7.09 (q, J=7.3 Hz, 1H), 6.75-6.56 (m, 3H), 5.40-5.20 (m, 2H), 4.80-4.57 (m, 1H), 4.49-4.31 (m, 1H), 3.98-3.82 (m, 1H), 3.47-3.15 (m, 4H), 3.15-2.95 (m, 2H), 2.38-2.22 (m, 1H), 2.11 (s, 1H). HRMS (ESI-QTOF) m/z: calculated for C$_{26}$H$_{26}$BrN$_4$O$_5{}^+$ [M+H]$^+$ 553.10811. found 553.10726.

(2S,4S)-quinolin-3-ylmethyl 2-((((S)-3-bromo-4,5-dihydroisoxazol-5-yl)methyl)carbamoyl)-4-(4-hydroxyphenyl)pyrrolidine-1-carboxylate (12)

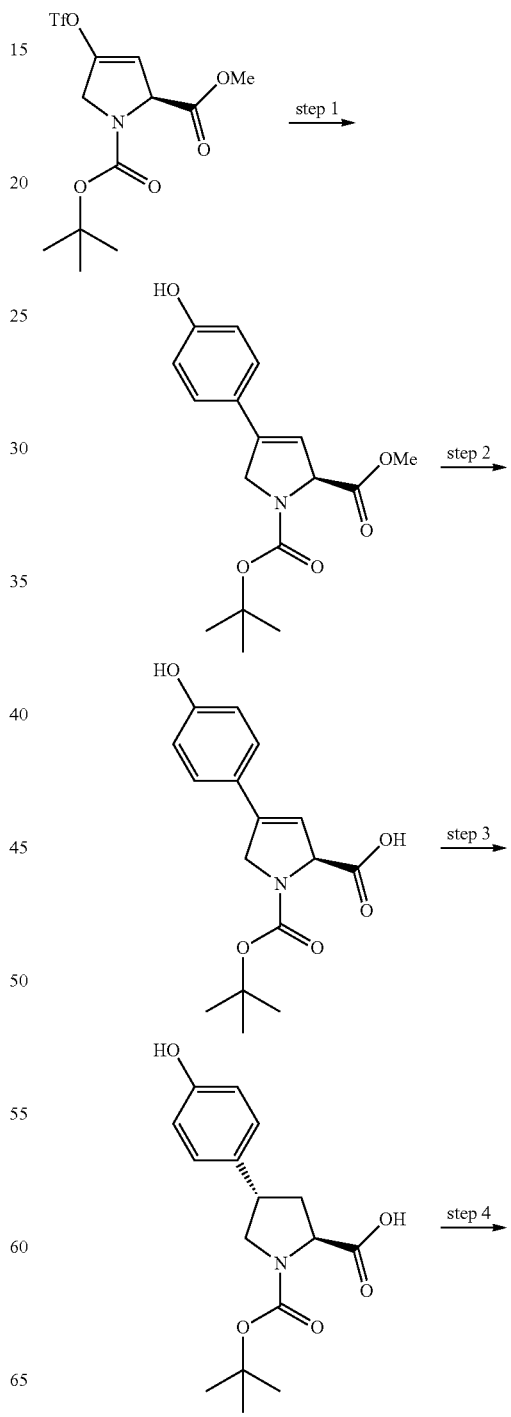

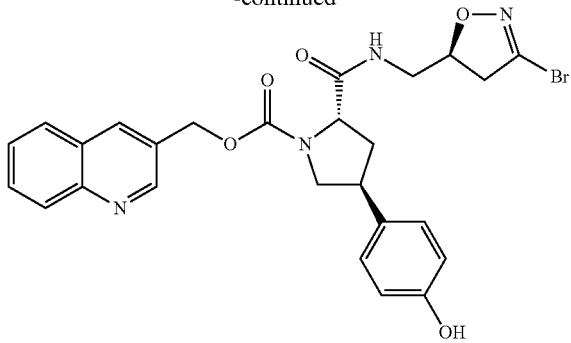

Step 1—(S)-1-tert-butyl 2-methyl 4-(4-hydroxyphenyl)-1H-pyrrole-1,2(2H,5H)-dicarboxylate: Adapting a procedure from the patent literature by Nakai and coworkers (Nakai et al., 2002 EP1535906A1), (4-hydroxyphenyl)boronic acid (0.367 g, 2.66 mmol) and Tetrakis(triphenylphosphine) palladium(0) (0.308 g, 0.266 mmol) were placed in a 50 mL round bottom flask and dissolved in 20 mL dioxane. Then, (S)-1-tert-butyl 2-methyl 4-((((trifluoromethyl)sulfonyl)oxy)-1H-pyrrole-1,2(2H,5H)-dicarboxylate (1 g, 2.66 mmol), prepared as described in the literature reference, was added, followed by potassium carbonate (4.00 ml, 7.99 mmol) as an aqueous solution. The mixture was placed in an oil-bath that had been preheated to 80° C. and stirred for 20 minutes, by which time the solution had turned from orange to dark black, indicating completion. The solution was concentrated under reduced pressure and then diluted with water (50 mL). Aqueous HCl was added to adjust the pH to approximately 5. The mixture was extracted with ethyl acetate (2*50 mL) and the combined organic extracts were dried and then filtered through a plug of silica. Removal of the volatiles furnished a grey crude product that was purified by silica gel chromatography in 10-25% ethyl acetate in pentane to yield (S)-1-tert-butyl 2-methyl 4-(4-hydroxyphenyl)-1H-pyrrole-1,2(2H,5H)-dicarboxylate (0.484 g, 1.516 mmol, 56.9% yield). ($R_f$ in 15% ethyl acetate in pentane approx. 0.15). $^1$H NMR (500 MHz, DMSO-$d_6$, mixture of rotational isomers) δ 9.72 (s, 1H), 7.32 (dd, J=8.7, 6.9 Hz, 2H), 6.79-6.72 (m, 2H), 6.08 (m, 1H), 5.02 (dt, J=5.2, 2.7 Hz, 1H), 4.4 (ddt, J=9.5, 4.6, 2.1 Hz, 2H), 3.68 & 3.65 (2 s, 3H), 1.44 & 1.36 (2 s, 9H).

Step 2—(S)-1-(tert-butoxycarbonyl)-4-(4-hydroxyphenyl)-2,5-dihydro-1H-pyrrole-2-carboxylic acid: (S)-1-tert-butyl 2-methyl 4-(4-hydroxyphenyl)-1H-pyrrole-1,2(2H,5H)-dicarboxylate (484 mg, 1.516 mmol) was dissolved in THF (40 mL) and methanol (20 mL). To the stirred solution, 20 mL of LiOH (1M in water) was added and the reaction monitored by TLC (50% EtOAc/pentane). Then, an equimolar amount of 1 M hydrochloric acid was added and the volatiles were removed under reduced pressure. The residue was taken up in additional water (50 mL final volume), the pH adjusted to 3-4 using hydrochloric acid and the aqueous phase extracted with ethyl acetate (3*50 mL). The combined extracts were dried over sodium sulfate and the solvent evaporated, yielding (S)-1-(tert-butoxycarbonyl)-4-(4-hydroxyphenyl)-2,5-dihydro-1H-pyrrole-2-carboxylic acid (431 mg, 1.412 mmol, 93% yield) as an off-white foam that was used without further purification.

Step 3—(2S,4S)-1-(tert-butoxycarbonyl)-4-(4-hydroxyphenyl)pyrrolidine-2-carboxylic acid: Under an atmosphere of argon, (S)-1-(tert-butoxycarbonyl)-4-(4-hydroxyphenyl)-2,5-dihydro-1H-pyrrole-2-carboxylic acid (431 mg, 1.412 mmol) and Chlorotris(triphenylphosphine)rhodium(I) (131 mg, 0.141 mmol) were dissolved in anhydrous THF (24 mL) and methanol (24 mL) and Triethylamine (198 μl, 1.412 mmol) added. The atmosphere in the flask was then changed to hydrogen and a slight positive pressure maintained while the solution was stirred overnight. The volatiles were then evaporated and the residue suspended in sodium bicarbonate (100 mL) and the pH adjusted to approximately 10 with 1 M aqueous sodium hydroxide. Ethyl Acetate (100 mL) was then added and the mixture partitioned. The organic layer was washed with another 50 mL of sodium bicarbonate solution and the combined aqueous layers were brought to pH 3-4 using 1 M aqueous hydrochloric acid and the product subsequently backextracted with ethyl acetate (3*100 mL). The combined organic layers were dried over sodium sulfate and evaporated to furnish (2S,4S)-1-(tert-butoxycarbonyl)-4-(4-hydroxyphenyl)pyrrolidine-2-carboxylic acid (384 mg, 1.249 mmol, 89% yield) as an off-white foam in good purity. $^1$H NMR (400 MHz, Methanol-$d_4$, mixture of rotational isomers) δ 7.08 (d, J=8.4 Hz, 2H), 6.74 (d, J=8.5 Hz, 2H), 4.41 & 4.37 (2 dd, J=8.9, 2.2 Hz, 1H), 3.86 (ddd, J=12.5, 10.2, 7.7 Hz, 1H), 3.50-3.38 (m, 1H), 3.34-3.26 (m, 1H, partly obscured by solvent), 2.44-2.33 (m, 1H), 2.29 (ddd, J=13.1, 6.8, 2.6 Hz, 1H), 1.47 & 1.44 (2 s, 9H).

Step 4—(2S,4S)-quinolin-3-ylmethyl 2-((((S)-3-bromo-4,5-dihydroisoxazol-5-yl)methyl) carbamoyl)-4-(4-hydroxyphenyl)pyrrolidine-1-carboxylate: The amino acid was elaborated into the final inhibitor using the general procedure. $^1$H NMR (500 MHz, DMSO-$d_6$) δ 9.31 (s, 1H), 8.93 & 8.86 (2 d, J=2.1 Hz, 1H), 8.40 & 8.33 (2 t, J=6.1 Hz, 1H), 8.35 & 8.26 (2 d, J=1.1 Hz, 1H), 7.77 (ddd, J=8.4, 6.9, 1.5 Hz, 1H), 7.63 (dddd, J=8.1, 6.9, 4.1, 1.2 Hz, 1H), 7.07 (dd, J=8.7, 2.7 Hz, 2H), 6.69 (t, J=8.1 Hz, 2H), 5.35-5.19 (m, 2H), 4.79-4.71 & 4.66-4.59 (2 m, 1H), 4.44 & 4.35 (dd, J=8.8, 2.0 Hz, 1H), 3.91 & 3.84 (2 dd, J=9.5, 7.3 Hz, 1H), 3.45-3.18 (m, 5H), 3.03 (ddd, J=25.1, 17.6, 7.2 Hz, 1H), 2.28 (dtd, J=24.4, 12.2, 9.0 Hz, 1H), 2.13-2.01 (m, 1H). HRMS (ESI-QTOF) m/z: calculated for $C_{26}H_{26}BrN_4O_5^+$ [M+H]$^+$ 553.10811. found 553.10784.

(2S,4S)-quinolin-3-ylmethyl 2-((((S)-3-bromo-4,5-dihydroisoxazol-5-yl)methyl)carbamoyl)-4-(3-chlorophenyl)pyrrolidine-1-carboxylate, TFA salt (13). The title compound was prepared analogously to compound (12) but with one equivalent of HBTU in place of EDC HCl and HOBt as the amide coupling reagent in step 4 and purified by reverse phase HPLC, furnishing the title compound as its TFA salt. $^1$H NMR (500 MHz, DMSO-$d_6$, mixture of rotational isomers) δ 9.01 & 8.92 (2 s, 1H), 8.51-8.30 (m, 2H), 8.11-7.99 (m, 2H), 7.83 (dd, J=8.5, 6.7 Hz, 1H), 7.74-7.65 (m, 1H), 7.39 (s, 1H), 7.38-7.24 (m, 3H), 5.43-5.21 (m, 2H), 4.80-4.58 (m, 1H), 4.45 & 4.36 (2 t, J=9.0 & 8.3 Hz, 1H), 4.03-3.89 (m, 1H), 3.59-3.17 (m, 5H), 3.15-2.94 (m, 1H), 2.45-2.28 (m, 1H), 2.23-2.08 (m, 1H). HRMS (ESI-QTOF) m/z: calculated for $C_{26}H_{26}BrClN_4O_4^+$ [M+H]$^+$ 571.07422. found 571.07174.

(2S,4S)-quinolin-3-ylmethyl 2-((((S)-3-bromo-4,5-dihydroisoxazol-5-yl)methyl)carbamoyl)-4-(4-chlorophenyl)pyrrolidine-1-carboxylate, TFA salt (14). The title compound was prepared analogously to compound (12) but with one equivalent of HBTU in place of EDC HCl and HOBt as the amide coupling reagent in step 4 and purified by reverse phase HPLC, furnishing the title compound as its TFA salt. $^1$H NMR (500 MHz, DMSO-$d_6$, mixture of rotational isomers) δ 9.01 & 8.93 (2 d, J=2.1 Hz, 1H), 8.53-8.32 (m, 2H), 8.14-7.99 (m, 2H), 7.84 (dd, J=8.6, 6.8 Hz, 1H), 7.70 (td, J=7.6, 2.8 Hz, 1H), 7.41-7.28 (m, 4H), 5.41-5.22 (m, 2H), 4.82-4.57 (m, 1H), 4.46 & 4.37 (t, J=9.4 & 8.8 Hz, 1H), 4.04-3.87 (m, 1H), 3.56-3.17 (m, 5H), 3.17-2.94 (m, 1H), 2.35 (ddd, J=23.1, 19.6, 10.5 Hz, 1H), 2.22-2.07 (m, 1H). HRMS (ESI-QTOF) m/z: calculated for $C_{26}H_{26}BrClN_4O_4^+$ [M+H]$^+$ 571.07422. found 571.07327.

(2S,4S)-quinolin-3-ylmethyl 2-((((S)-3-bromo-4,5-dihydroisoxazol-5-yl)methyl)carbamoyl)-4-(5-fluoro-1H-indol-3-yl)pyrrolidine-1-carboxylate, TFA salt (15). Tert-butyl 5-fluoro-3-iodo-1H-indole-1-carboxylate was prepared from 5-fluoroindole using the procedure reported by Tasch and coworkers (Tasch et al., 2011) and then subjected to the Masuda borylation conditions described in the same report, except that 2 equivalents of pinacolborane were used. One hour after initiating the borylation reaction, all components for the Suzuki coupling reaction as described in step 1 of compound (12), including another aliquot of catalyst were added to the hot reaction mixture. The remainder of the synthesis also followed the procedure outlined for compound (12) but with one equivalent of HBTU in place of EDC HCl and HOBt as the amide coupling reagent in step 4. The crude product was purified by reverse-phase HPLC, furnishing the product as its TFA salt. $^1$H NMR (400 MHz, DMSO-d$_6$) δ 11.04 (s, 1H), 9.00 & 8.92 (2 d, J=2.1 Hz, 1H), 8.48-8.28 (m, 2H), 8.11-7.98 (m, 2H), 7.89-7.78 (m, 1H), 7.68 (q, J=7.5 Hz, 1H), 7.39-7.27 (m, 3H), 7.01-6.83 (m, 1H), 5.42-5.20 (m, 2H), 4.82-4.59 (m, 1H), 4.53-4.33 (m, 1H), 4.09-3.88 (m, 1H), 3.74-3.57 (m, 1H), 3.55-3.44 (m, 1H), 3.44-3.19 (m, 3H), 3.15-2.95 (m, 1H), 2.47-2.33 (m, 1H), 2.27-2.11 (m, 1H). HRMS (ESI-QTOF) m/z: calculated for $C_{28}H_{26}BrFN_5O_4^+$ [M+H]$^+$ 594.11467. found 594.11386.

(S)-quinolin-3-ylmethyl 2-((((S)-3-bromo-4,5-dihydroisoxazol-5-yl)methyl)carbamoyl)-4-phenyl-2,5-dihydro-1H-pyrrole-1-carboxylate, TFA salt (16). (S)-1-tert-butyl 2-methyl 4-phenyl-1H-pyrrole-1,2(2H,5H)-dicarboxylate was prepared analogously to step 1 of compound (12). The remainder of the synthesis followed a reversed sequence. An aliquot of the intermediate (100 mg, 0.33 mmol) was deprotected using 4M HCl in dioxane for 30 minutes. The solvent was carefully evaporated and the residue redissolved in methanol and evaporated again. The HCl salt thus obtained was coupled to quinolin-3-ylmethyl 1H-imidazole-1-carboxylate analogously to step 3 of the general procedure, furnishing (S)-2-methyl 1-(quinolin-3-ylmethyl) 4-phenyl-1H-pyrrole-1,2(2H,5H)-dicarboxylate which was purified by preparative TLC. The methyl ester was saponified analogously to step 2 of compound (12) and the free acid eventually coupled to (S)-(3-bromo-4,5-dihydroisoxazol-5-yl)methanamine as described in step 1 of the general procedure but with one equivalent of HBTU in place of EDC and HOBt as the coupling reagent. Reverse-phase HPLC, furnished the compound as its TFA salt. $^1$H NMR (400 MHz, DMSO-d$_6$, mixture of rotational isomers) δ 9.06 & 8.94 (2 d, J=2.2 Hz, 1H), 8.54 & 8.43 (2 s, 1H), 8.53-8.44 (m, 1H), 8.12-8.00 (m, 2H), 7.84 (t, J=7.4 Hz, 1H), 7.69 (t, J=7.5 Hz, 1H), 7.56-7.47 (m, 1H), 7.43-7.29 (m, 2H), 6.32-6.21 (m, 1H), 5.47-5.25 (m, 2H), 5.21-5.04 (m, 1H), 4.78-4.52 (m, 3H), 3.45-2.88 (m, 4H). HRMS (ESI-QTOF) m/z: calculated for $C_{26}H_{24}BrN_4O_4^+$ [M+H]$^+$ 535.09754. found 535.09660.

Example 2

Clinical Trial Using TG2 Inhibitors on Inflammation in Patients with Sepsis

Purpose: Sepsis is a clinical syndrome which infection trigger systemic inflammatory response. Uncontrolled inflammatory process leads to multiple organ dysfunction and cause early mortality in severe sepsis. The purpose of this study is to determine effects of TG2 Inhibitors disclosed herein on inflammation in severe sepsis patients.

Study Type: Interventional

Study Allocation: Randomized

Design: Endpoint Classification: Efficacy Study

Intervention Model: Parallel Assignment

Masking: Double Blind (Subject, Caregiver, Investigator, Outcomes Assessor)

Primary Purpose: Treatment

Primary Outcome Measures:

Inflammation [Time Frame: 3 days]

Determine effects of TG2 inhibitor treatment on nuclear factor kappa B, inhibitor kappa B kinase and tumor necrosis factor-alpha.

Secondary Outcome Measures:

Clinical outcome [Time Frame: 14 days]

Determine impact of TG2 inhibitors on mortality and improvement APACHE II score

Eligibility

Ages Eligible for Study: 18 Years to 90 Years

Genders Eligible for Study: Both

Accepts Healthy Volunteers: No

Criteria

Inclusion Criteria:

Patients with severe sepsis and septic shock define by revised Sepsis Criteria (2001)

Within 48 hour diagnose sepsis

Agree to participate

Exclusion Criteria:

Pregnancy and lactation

Severe thrombocytopenia, platelet less than 30.000/mm3

Bleeding or high risk of major bleeding

During anticoagulant treatment

After thrombolytic treatment

Decompensated chronic liver diseases

Chronic kidney diseases on dialysis treatment

During high dose corticosteroid treatment

HIV with CD4 count below 50/mm3

These and other methods of the invention can be practiced using the methods provided by the invention.

All publications, patents, and patent applications cited in this specification are herein incorporated by reference as if each individual publication, patent, or patent application were specifically and individually indicated to be incorporated by reference.

The present invention has been described in terms of particular embodiments found or proposed by the inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in methods, structures, and compounds without affecting the biological action in kind or amount. All such modifications are intended to be included within the scope of the appended claims.

What is claimed is:

1. An isolated compound having a structure:

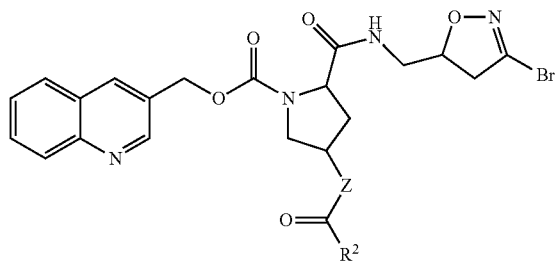

wherein:
Z is O or NH or NCH$_3$; and
R$^2$ is optionally substituted aryl or optionally substituted heteroaryl.

2. An isolated compound having a structure:

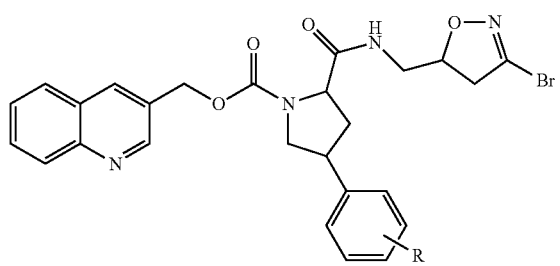

wherein:
R is halogen, OR$^1$, CN, C$_1$-C$_6$alkyl; and
R$^1$ is H, C$_1$-C$_6$alkyl, or C$_3$-C$_8$cycloalkyl.

3. An isolated compound having a structure:

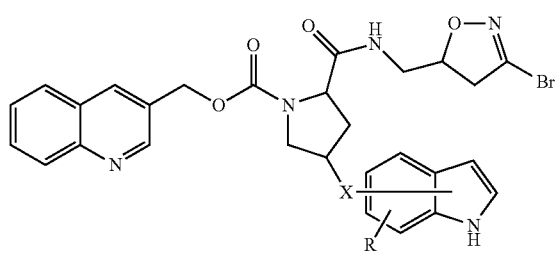

wherein
X is a bond;
R is halogen, OR$^1$, CN, C$_1$-C$_6$alkyl; and
R$^1$ is H, C$_1$-C$_6$alkyl, or C$_3$-C$_8$cycloalkyl.

4. An isolated compound having a structure:

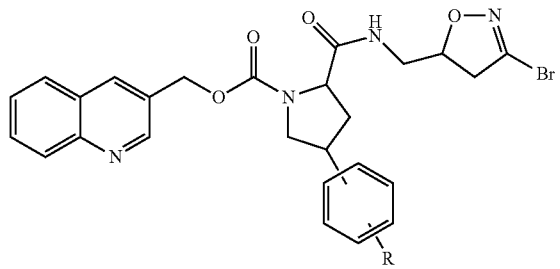

wherein
R is halogen, OR$^1$, CN, C$_1$-C$_6$alkyl; and
R$^1$ is H, C$_1$-C$_6$alkyl, or C$_3$-C$_8$cycloalkyl.

5. An isolated compound selected from:
(2S,4R)-quinolin-3-ylmethyl 4-benzamido-2-((((S)-3-bromo-4,5-dihydroisoxazol-5-yl)methyl)carbamoyl) pyrrolidine-1-carboxylate; (2S,4R)-quinolin-3-ylmethyl 2-((((S)-3-bromo-4,5-dihydroisoxazol-5-yl) methyl) carbamoyl)-4-(2-hydroxybenzamido) pyrrolidine-1-carboxylate; (2S,4R)-quinolin-3-ylmethyl 2-((((S)-3-bromo-4,5-dihydroisoxazol-5-yl) methyl) carbamoyl)-4-(3-hydroxybenzamido) pyrrolidine-1-carboxylate; (2S,4R)-quinolin-3-ylmethyl 2-((((S)-3-bromo-4,5-dihydroisoxazol-5-yl) methyl) carbamoyl)-4-(4-hydroxybenzamido) pyrrolidine-1-carboxylate; (2S,4R)-quinolin-3-ylmethyl 2-((((S)-3-bromo-4,5-dihydroisoxazol-5-yl) methyl)carbamoyl)-4-(nicotinamido)pyrrolidine-1-carboxylate; (2S,4R)-quinolin-3-ylmethyl 2-((((S)-3-bromo-4,5-dihydroisoxazol-5-yl)methyl) carbamoyl)-4-(pyrazine-2-carboxamido)pyrrolidine-1-carboxylate; 1-(((3R,5S)-5-((((S)-3-bromo-4,5-dihydroisoxazol-5-yl)methyl)carbamoyl)-1-((quinolin-3-ylmethoxy)carbonyl)pyrrolidin-3-yl)carbamoyl) cyclobutanecarboxylic acid; (2S,4S)-quinolin-3-ylmethyl 2-((((S)-3-bromo-4,5-dihydroisoxazol-5-yl)methyl)carbamoyl)-4-phenylpyrrolidine-1-carboxylate; (2S,4R)-quinolin-3-ylmethyl 2-((((S)-3-bromo-4,5-dihydroisoxazol-5-yl)methyl)carbamoyl)-4-phenylpyrrolidine-1-carboxylate; (2S,4S)-quinolin-3-ylmethyl 2-((((S)-3-bromo-4,5-dihydroisoxazol-5-yl)methyl)carbamoyl)-4-(2-hydroxyphenyl)pyrrolidine-1-carboxylate; (2S,4S)-quinolin-3-ylmethyl 2-((((S)-3-bromo-4,5-dihydroisoxazol-5-yl)methyl) carbamoyl)-4-(3-hydroxyphenyl)pyrrolidine-1-carboxylate; (2S,4S)-quinolin-3-ylmethyl 2-((((S)-3-bromo-4,5-dihydroisoxazol-5-yl)methyl) carbamoyl)-4-(4-hydroxyphenyl)pyrrolidine-1-carboxylate; (2S,4S)-quinolin-3-ylmethyl 2-((((S)-3-bromo-4,5-dihydroisoxazol-5-yl)methyl) carbamoyl)-4-(3-chlorophenyl)pyrrolidine-1-carboxylate; (2S,4S)-quinolin-3-ylmethyl 2-((((S)-3-bromo-4,5-dihydroisoxazol-5-yl)methyl) carbamoyl)-4-(4-chlorophenyl)pyrrolidine-1-carboxylate; (2S,4S)-quinolin-3-ylmethyl 2-((((S)-3-bromo-4,5-dihydroisoxazol-5-yl)methyl)carbamoyl)-4-(5-fluoro-1H-indol-3-yl)pyrrolidine-1-carboxylate; (S)-quinolin-3-ylmethyl 2-((((S)-3-bromo-4,5-dihydroisoxazol-5-yl)methyl) carbamoyl)-4-phenyl-2,5-dihydro-1H-pyrrole-1-carboxylate.

6. An isolated compound (2S,4R)-quinolin-3-ylmethyl 2-((((S)-3-bromo-4,5-dihydroisoxazol-5-yl)methyl)carbamoyl)-4-(nicotinamido)pyrrolidine-1-carboxylate.

7. A pharmaceutical formulation comprising a compound according to claim 1 or claim 5, and a pharmaceutically acceptable excipient.

8. A pharmaceutical formulation of claim 7, in a unit dosage form.

9. A pharmaceutical formulation of claim 8, comprising a dose effective to inhibit undesirable tissue transglutaminase 2 activity.

10. A pharmaceutical formulation of claim 7, further comprising a second pharmaceutically active agent.

11. A method of reducing inflammation associated with TG2 activity in an individual, the method comprising:
administering a pharmaceutical formulation according to claim 7 to an individual suffering from inflammation associated with TG2 activity.

12. The method of claim 11, further comprising administering an effective dose of thioredoxin to said individual.

* * * * *